United States Patent [19]

Shinjo et al.

[11] Patent Number: 5,238,601

[45] Date of Patent: Aug. 24, 1993

[54] FERROELECTRIC CHIRAL SMECTIC LIQUID CRYSTAL COMPOSITION AND LIQUID CRYSTAL DEVICE USING SAME

[75] Inventors: Kenji Shinjo, Atsugi; Takao Takiguchi, Tokyo; Hiroyuki Kitayama, Sagamihara; Kazuharu Katagiri, Tama; Masahiro Terada, Atsugi; Takeshi Togano, Yokohama; Masataka Yamashita, Hiratsuka, all of Japan

[73] Assignee: Canon Kabushiki Kaisha, Tokyo, Japan

[21] Appl. No.: 370,909

[22] Filed: Jun. 23, 1989

[30] Foreign Application Priority Data

Jun. 24, 1988 [JP] Japan ................................ 63-157675
Jul. 18, 1988 [JP] Japan ................................ 63-180021

[51] Int. Cl.$^5$ ...................... C09K 19/30; C09K 19/34; C09K 19/12; G02F 1/13
[52] U.S. Cl. ......................... 252/299.63; 252/299.61; 252/299.66; 359/103
[58] Field of Search ...................... 252/299.61, 299.63, 252/299.66; 359/103

[56] References Cited

U.S. PATENT DOCUMENTS

| | | | |
|---|---|---|---|
| 4,622,162 | 11/1986 | Kimura et al. | 252/299.5 |
| 4,708,441 | 11/1987 | Petrzilka et al. | 350/346 |
| 4,729,847 | 3/1988 | Miyazawa et al. | 252/299.64 |
| 4,751,019 | 6/1988 | Saito et al. | 252/299.66 |
| 4,816,181 | 3/1989 | Miyazawa et al. | 252/299.65 |
| 4,846,998 | 7/1989 | Pohl et al. | 252/299.63 |
| 4,867,903 | 9/1989 | Nohira et al. | 252/299.61 |
| 4,871,472 | 10/1989 | Krause et al. | 252/299.65 |
| 4,917,821 | 11/1988 | Mori et al. | 252/299.63 |
| 4,946,989 | 8/1990 | Kawamura et al. | 560/51 |

FOREIGN PATENT DOCUMENTS

| | | |
|---|---|---|
| 0267585 | 5/1988 | European Pat. Off. |
| 0315958 | 5/1989 | European Pat. Off. |
| 0335348 | 10/1989 | European Pat. Off. |
| WO0005013 | 8/1987 | PCT Int'l Appl. |
| 8707890 | 12/1987 | PCT Int'l Appl. |

*Primary Examiner*—Robert L. Stoll
*Assistant Examiner*—C. Harris
*Attorney, Agent, or Firm*—Fitzpatrick, Cella, Harper & Scinto

[57] ABSTRACT

A ferroelectric chiral smectic liquid crystal composition, comprising at least one optically active compound represented by the following formula (I):

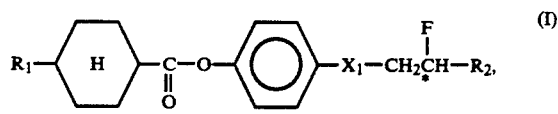

wherein $R_1$ denotes a linear alkyl group having 1-14 carbon atoms; $R_2$ denotes a linear or branched alkyl group having 1-14 carbon atoms capable of having a subtituent; and $X_1$ denotes a single bond,

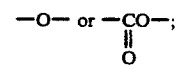

and at least one compound represented by the following formula (II):

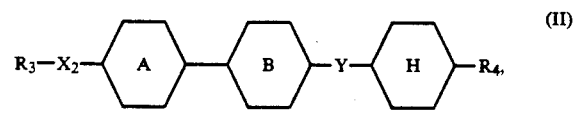

wherein $R_3$ denotes a linear or branched alkyl group having 1-18 carbon atoms capable of having a substituent; $R_4$ denotes a linear alkyl group having 1-10 carbon atoms; $X_2$ denotes a single bond, (Abstract continued on next page.)

-continued
and 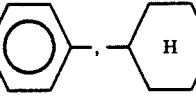 and 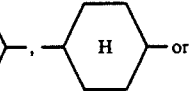
respectively denote 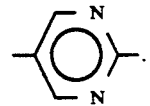
7 Claims, 3 Drawing Sheets

FERROELECTRIC CHIRAL SMECTIC LIQUID CRYSTAL COMPOSITION AND LIQUID CRYSTAL DEVICE USING SAME

FIELD OF THE INVENTION AND RELATED ART

The present invention relates to a liquid crystal composition used in a liquid crystal display device, a liquid crystal-optical shutter, etc., more particularly to a novel liquid crystal composition with improved responsiveness to an electric field and a liquid crystal device using the liquid crystal composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4367924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. A high response speed can be obtained by (a) increasing the spontaneous polarization, (b) lowering the viscosity $\eta$, or (c) increasing the applied voltage. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°–40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

In a representative FLC cell structure, a pair of substrates are disposed, each substrate of e.g. glass being provided with an electrode pattern of e.g. ITO, further thereon with a layer of e.g. $SiO_2$ (about 1000 Å) for preventing short circuit between the pair of substrates and further thereon with a film of e.g. polyimide (PI; such as SP-510, 710, . . . available from Toray K.K.) of about 500 Å in thickness, which is then treated for alignment control by rubbing with e.g. an acetate fiber-planted cloth. Such a pair of substrates are disposed opposite to each other so that their alignment control directions are symmetrical and the spacing between the substrates is held at 1–3 microns.

On the other hand, it is known that the ferroelectric liquid crystal molecules under such non-helical conditions are disposed in succession so that their directors (longer molecular axes) are gradually twisted between the substrates and do not show a uniaxial orientation or alignment (i.e., in a splay alignment state). A problem in this case is a low transmittance through the liquid crystal layer.

Transmitted light intensity I through a liquid crystal is given by the following equation with respect to the incident light intensity $I_0$ under cross nicols when the uniaxial alignment of the molecules is assumed:

$$I = I_0 \sin^2(4\theta a) \sin^2(\pi \Delta n d / \lambda) \qquad (1),$$

wherein $\Delta n$ denotes the refractive index anisotropy of the FLC; d, the cell thickness; $\lambda$, the wavelength of the incident light; and $\theta a$, a half of the angle between two stable states (tilt angle).

When a conventional FLC cell is used, it has been experimentally known that $\theta a$ is 5–8 degrees under a twisted alignment condition. The control of physical properties affecting the term $\Delta n d \pi / \lambda$ cannot be easily performed, so that it is desired to increase $\theta a$ to increase I. However, this has not been successfully accomplished by only a static alignment technique.

With respect to such a problem, it has been proposed to utilize a torque relating to a dielectric anisotropy $\Delta \epsilon$ of an FLC (1983 SID report from AT & T; Japanese Laid-Open Patent Applns. 245142/1986, 246722/1986, 246723/1986, 246724/1986, 249024/1986 and 249025/1986). More specifically, a liquid crystal molecule having a negative $\Delta \epsilon$ tends to become parallel to the substrates under application of an electric field. By utilizing this property, if an effective value of AC electric field is applied even in a period other than switching, the above-mentioned twisted alignment is removed, so that $\theta a$ is increased to provide an increased transmittance (AC stabilization effect). A torque $\Gamma P_S$ acting on FLC molecules involved in switching of states and a torque $\Gamma \Delta \epsilon$ acting on FLC molecules relating to the AC stabilization effect are respectively proportional to physical properties as shown in the following formulas:

$$\Gamma P_S \alpha P_S \cdot E \qquad (2)$$

$$\Gamma \Delta \epsilon \alpha \tfrac{1}{2} \Delta \epsilon \cdot \epsilon_0 \cdot E^2 \qquad (3)$$

The above formula (3) apparently shows that the sign and absolute value of $\Delta \epsilon$ of the FLC play an important role.

FIG. 4 attached hereto shows the change of $\theta a$ versus Vrms experimentally measured for 4 FLCs having different values of $\Delta \epsilon$. The measurement was conducted under application of AC rectangular pulses of 60 KHz so as to remove the influence of $P_S$. The curves (A)–(D) correspond to the results obtained by using FLCs showing the following $\Delta \epsilon$ values (A) $\Delta \epsilon \approx -5.5$, \hfill (A)

(B) $\Delta \epsilon \approx -3.0$, \hfill (B)

(C) $\Delta \epsilon \approx -0$, \hfill (C)

(D) $\Delta \epsilon \approx 1.0$. \hfill (D)

As is clear from the graph in FIG. 8, a larger negative value of $\Delta \epsilon$ provides a large $\theta a$ at a lower voltage and thus contributes to provision of an increased I.

The transmittances obtained by using the liquid crystals (I) and (III) were 15% for (I) and 6% for (III) (under application of rectangular AC waveforms of 60 kHz and ±8 V), thus showing a clear difference.

As is known from the above examples, the display characteristics of an SSFLC (Surface-Stabilized FLC) can be remarkably changed by controlling the properties relating to $\Delta \epsilon$ and $P_S$.

In order to provide a ferroelectric liquid crystal composition having a negatively large $\Delta \epsilon$, it is most effective to include a compound having a negative $\Delta \epsilon$ with a large absolute value. For example, it is possible to obtain a compound having a negatively large $\Delta \epsilon$ by introducing a halogen or cyano group in a shorter axis direction of a molecule or by introducing a heterocyclic skeleton in a molecule.

The magnitude of $\Delta \epsilon$ of a compound having a negative $\Delta \epsilon$ substantially varies depending on the structure thereof. Some examples of such compounds are shown below:

$|\epsilon| \leq 2$

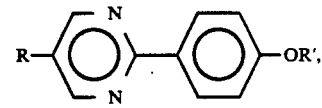

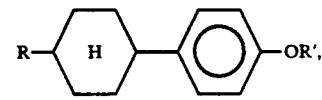

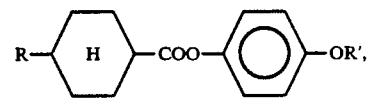

-continued

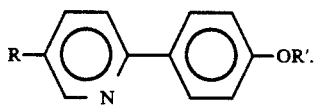

$2 < |\epsilon| \leq 5$

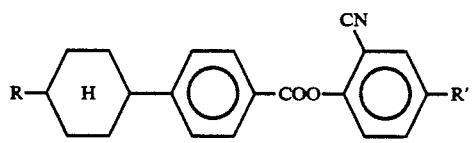

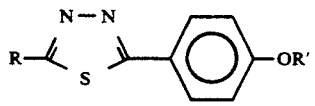

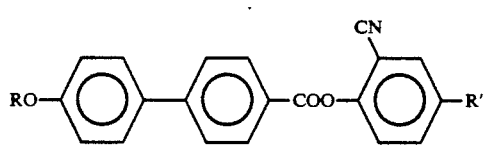

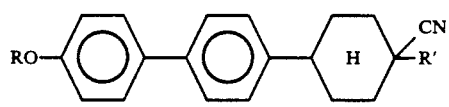

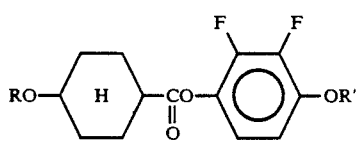

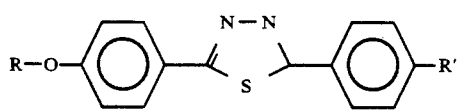

$5 < |\epsilon| \leq 10$

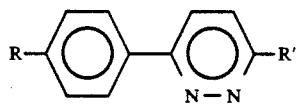

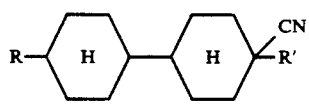

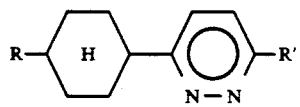

$|\epsilon| > 10$

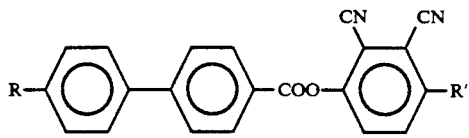

-continued

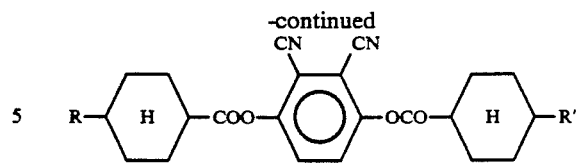

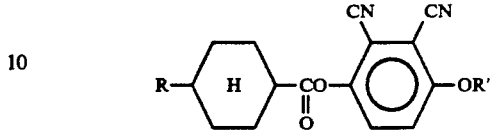

Herein, R and R' respectively denote an alkyl group. These may be classified roughly into three groups including compounds having a negatively small $\Delta\epsilon$ ($|\Delta\epsilon| \leq 2$), compounds having a negatively medium $\Delta\epsilon$ ($2 < |\Delta\epsilon| \leq 10$) and compounds having a negatively large $\Delta\epsilon$ ($|\Delta\epsilon| > 10$). Among these, compounds having a $|\Delta\epsilon|$ of $\leq 2$ have little effect of increasing $|\Delta\epsilon|$. Compounds having a $|\Delta\epsilon|$ of $>10$ are very effective in increasing $|\Delta\epsilon|$ increasing but those available heretofore are only dicyanohydroquinone derivatives.

However, a dicyanohydroquinone derivative, while it has a large $|\Delta\epsilon|$-increasing effect, has a high viscosity, so that it is liable to degrade a switching characteristic when its content is increased. On the other hand, among the compounds having a medium $|\Delta\epsilon|$ ($2 < |\Delta\epsilon| \leq 10$), some compounds have a moderately low viscosity while their $|\Delta\epsilon|$ increasing effect is somewhat lower than those having a large $|\Delta\epsilon|$.

From the above consideration, it is essential to select a compound having a negative anisotropy, preferably one having a $|\Delta\epsilon|$ of $>2$, and mixing it with an appropriately selected other compound in a properly selected mixing ratio.

SUMMARY OF THE INVENTION

An object of the present invention is to provide a chiral smectic liquid crystal composition having a large response speed and a decrease temperature-dependence of the response speed adapted for providing a practical ferroelectric liquid crystal device.

Another object of the present invention is to provide a liquid crystal composition further containing a mesomorphic compound having a negative dielectric anisotropy to show an AC stabilization effect providing remarkably improved display characteristics.

A further object of the present invention is to provide a liquid crystal device using such a liquid crystal composition and showing improved driving and display characteristics.

According to the present invention, there is provided a ferroelectric chiral smectic liquid crystal composition, comprising:

at least one optically active compound represented by the following formula (I):

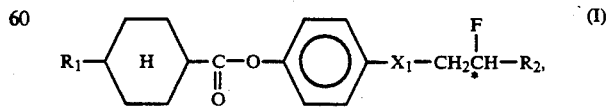

wherein $R_1$ denotes a linear alkyl group having 1-14 carbon atoms; $R_2$ denotes a linear or branched alkyl group having 1-14 carbon atoms capable of having a subtituent; and $X_1$ denotes a single bond,

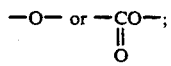

and
at least one compound represented by the following formula (II):

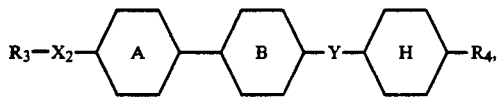

wherein $R_3$ denotes a linear or branched alkyl group having 1-18 carbon atoms capable of having a substituent; $R_4$ denotes a linear alkyl group having 1-10 carbon atoms; $X_2$ denotes a single bond, $-O-$, $-\underset{\underset{O}{\|}}{O}C-$, $-\underset{\underset{O}{\|}}{C}O-$ or $-O\underset{\underset{O}{\|}}{C}O-$; Y denotes $-\underset{\underset{O}{\|}}{O}C-$, $-\underset{\underset{O}{\|}}{C}O-$, $-CH_2O-$ or $-OCH_2-$; and —⟨A⟩— and —⟨B⟩— respectively denote —⟨○⟩—, —⟨H⟩— or —⟨N○N⟩—.

According to the present invention, there is further provided a ferroelectric liquid crystal composition as described above further comprising a mesomorphic compound having a negative dielectric anisotropy, which is preferably one having a $\Delta\epsilon < -2$, more preferably $\Delta\epsilon < -5$, most preferably $\Delta\epsilon < -10$.

The present invention further provides a liquid crystal device comprising a pair of substrates and such a ferroelectric liquid crystal composition as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
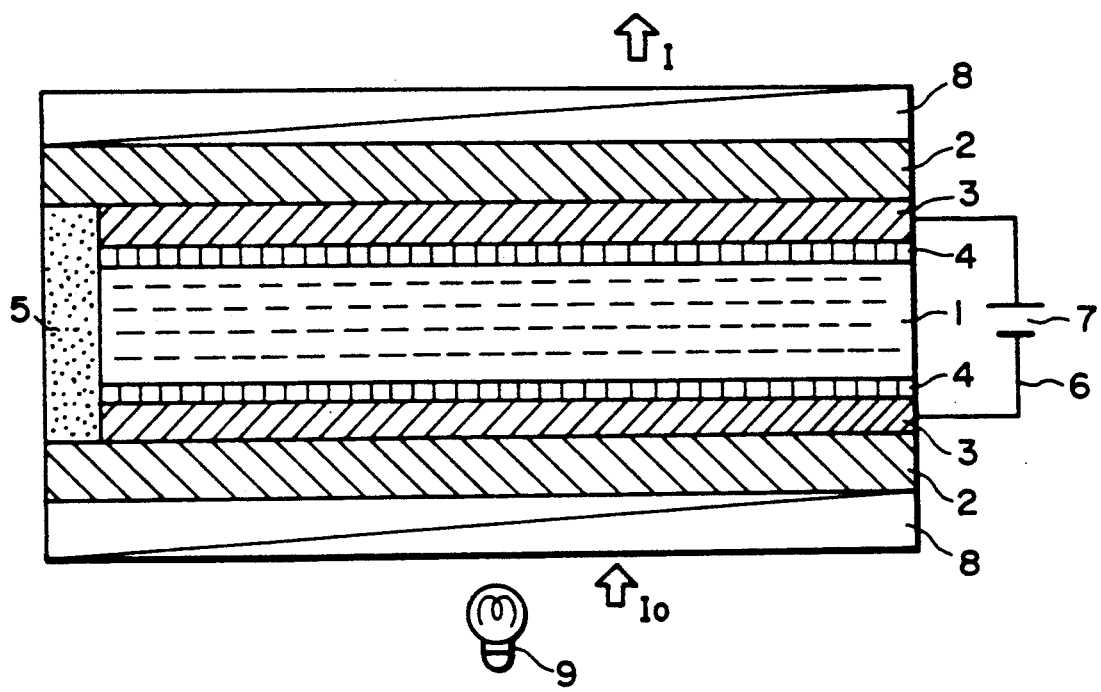
FIG. 1 is a schematic sectional view of a liquid crystal display device using a ferroelectric liquid crystal.

In the above-mentioned general formula (I), preferred example $X_1$ may include

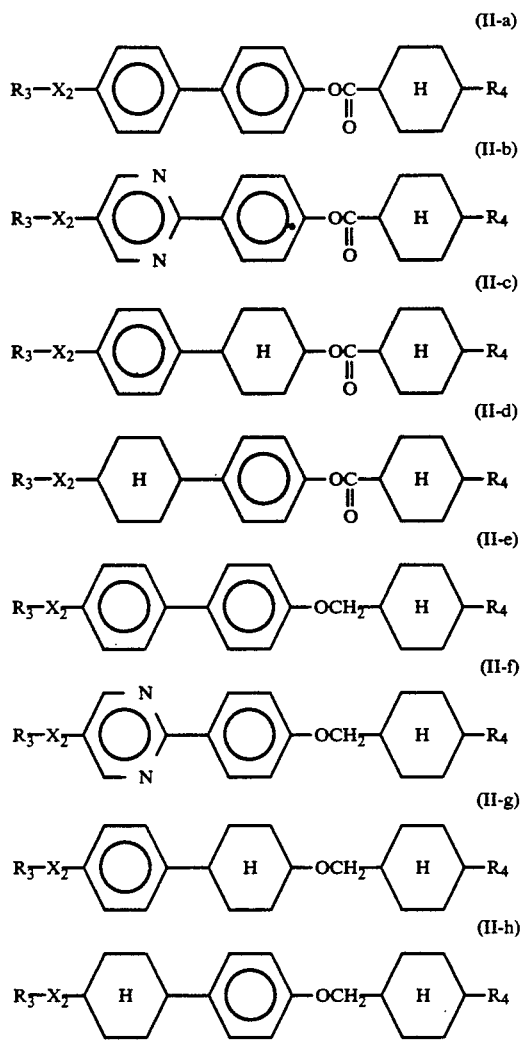

In the above-mentioned general formula (II), preferred examples of $R_2$ may include a linear alkyl group.

Further, preferred examples of the compounds represented by the above-mentioned general formula (II) may include those represented by the following formulas (II-a) to (II-h).

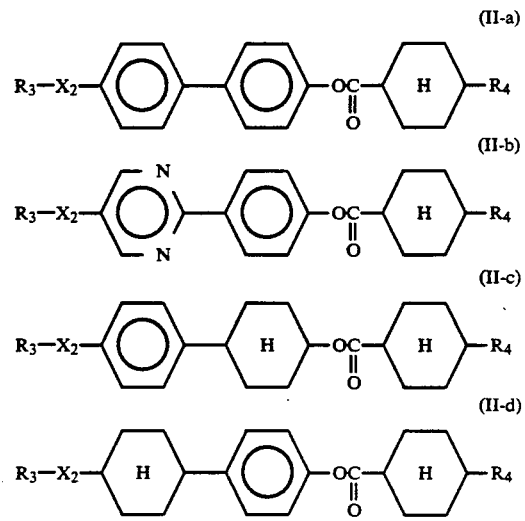

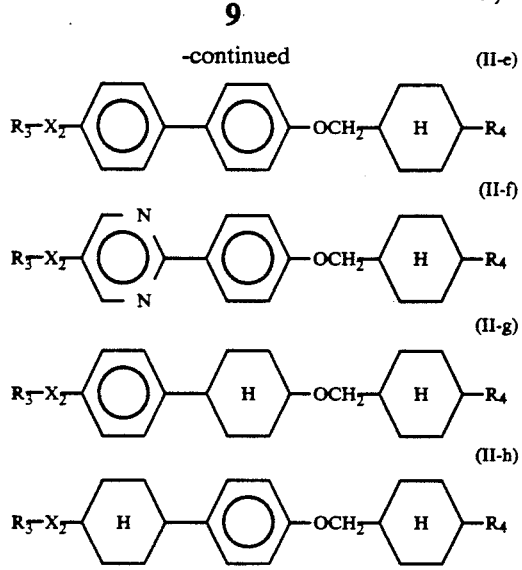
In the formulas (II-a) to (II-h), $R_3$, $R_4$ and $X_2$ are respectively the same as in the general formula (I). Preferred examples of $X_2$ may include a single bond,
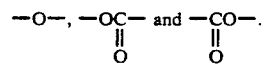
Specific examples of the compounds represented by the above-mentioned general formula (I) may include those shown by the following structural formulas.
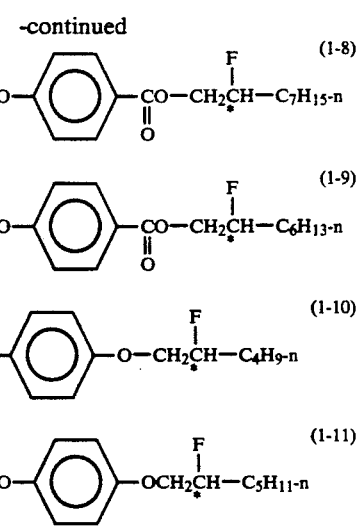
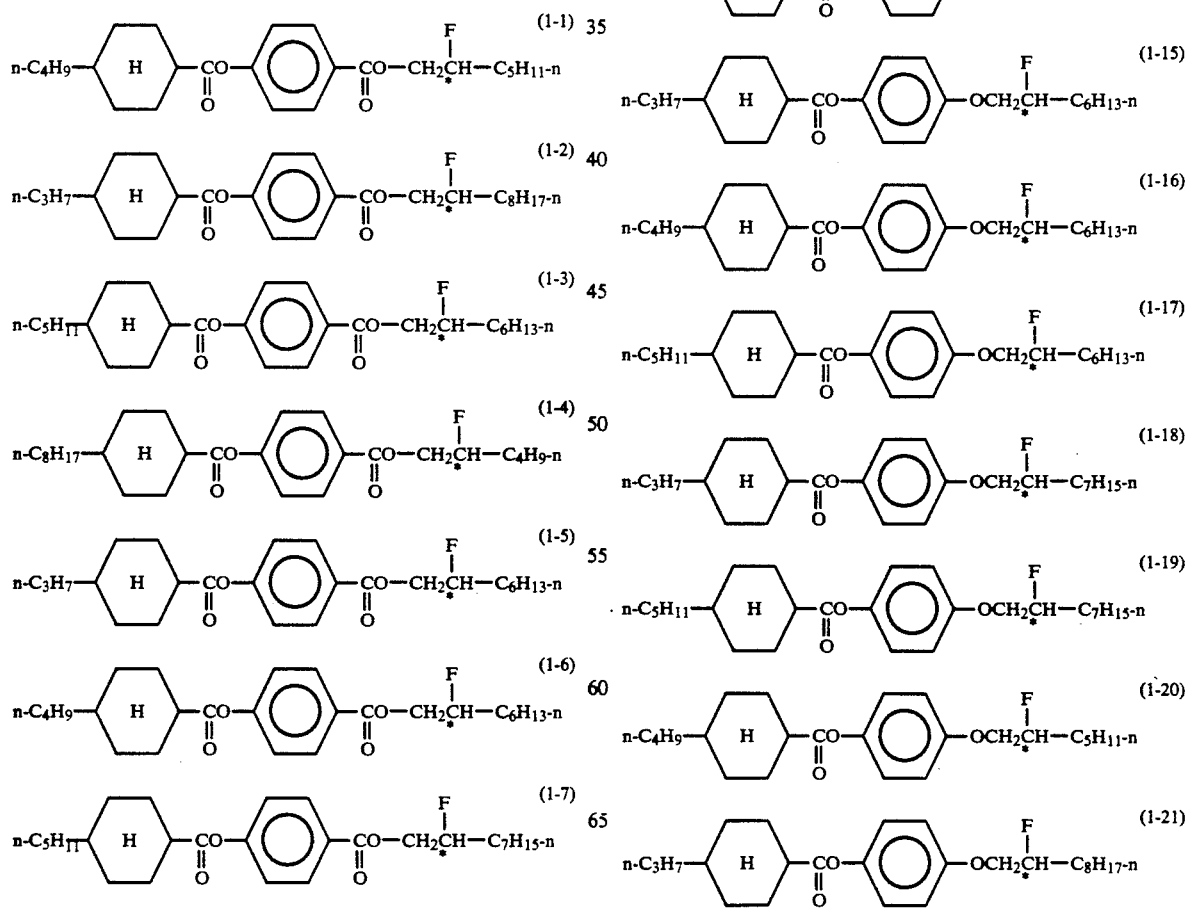

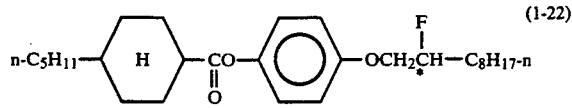
(1-22)

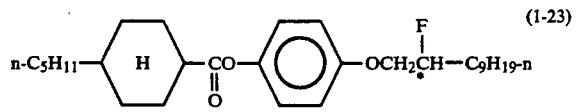
(1-23)

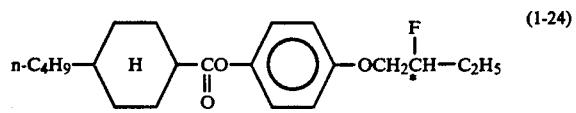
(1-24)

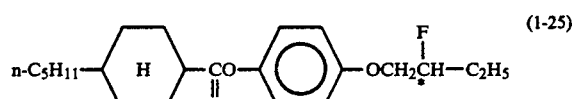
(1-25)

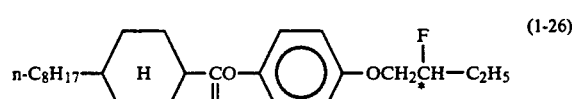
(1-26)

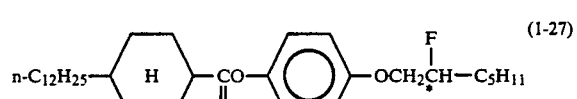
(1-27)

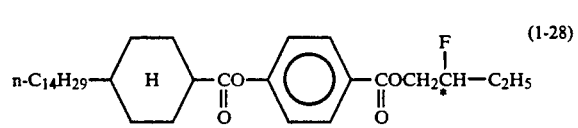
(1-28)

-continued
Reaction scheme

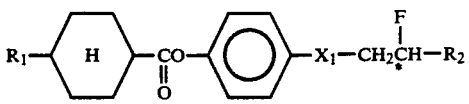

A representative example of synthesis of the compound represented by the general formula (I) is shown hereinbelow.

SYNTHESIS EXAMPLE 1

Synthesis of Compound Example 1-17

1.00 g (4.16 mM) of p-2-fluorooctyloxyphenol was dissolved in a mixture of 10 ml of pyridine and 5 ml of toluene, and a solution of 1.30 g (6.0 mM) of trans-4-n-pentylcyclohexanecarbonyl chloride was added dropwise thereto in 20–40 min. at below 5° C. After the addition, the mixture was stirred overnight at room temperature to obtain a white precipitate.

After the reaction, the reaction product was extracted with benzene, and the resultant benzene layer was washed with distilled water, followed by drying with magnesium sulfate and distilling-off of the benzene, purification by silica gel column chromatography and recrystallization from ethanol/methanol to obtain 1.20 g (2.85 mM) of trans-4-n-pentylcyclohexanecarboxylic acid-p-2-fluorooctyloxyphenyl-ester.

(Yield: 68.6%)

NMR data (ppm): 0.83–2.83 ppm (34H, m); 4.00–4.50 ppm (2H, q); 7.11 ppm (4H, s).

IR data ($cm^{-1}$): 3456, 2928, 2852, 1742, 1508, 1470, 1248, 1200, 1166, 1132, 854.

Phase transition temperature (°C.)

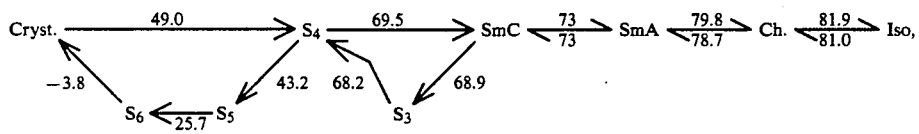

The compounds represented by the general formula (I) may be synthesized through the following reaction scheme.

Herein, the respective symbols denote the following phases, Iso.: isotropic phase, Ch.: cholesteric phase, SmA: smectic A phase, SmC: smectic C phase, $S_3$–$S_6$: phases of higher other than SmC or SmC* (chiral smectic C phase), and Cryst.: crystal phase.

Specific examples of the compounds represented by the above-mentioned general formula (II) may include those shown by the following structural formulas.

Reaction scheme

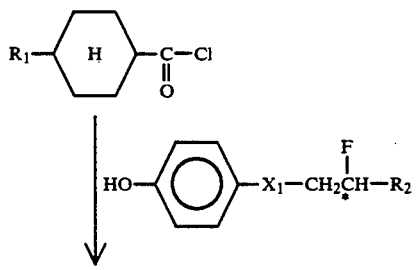

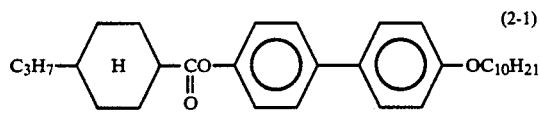
(2-1)

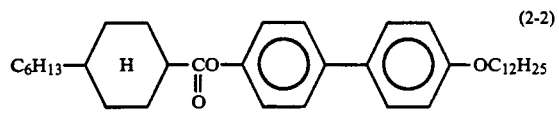
(2-2)

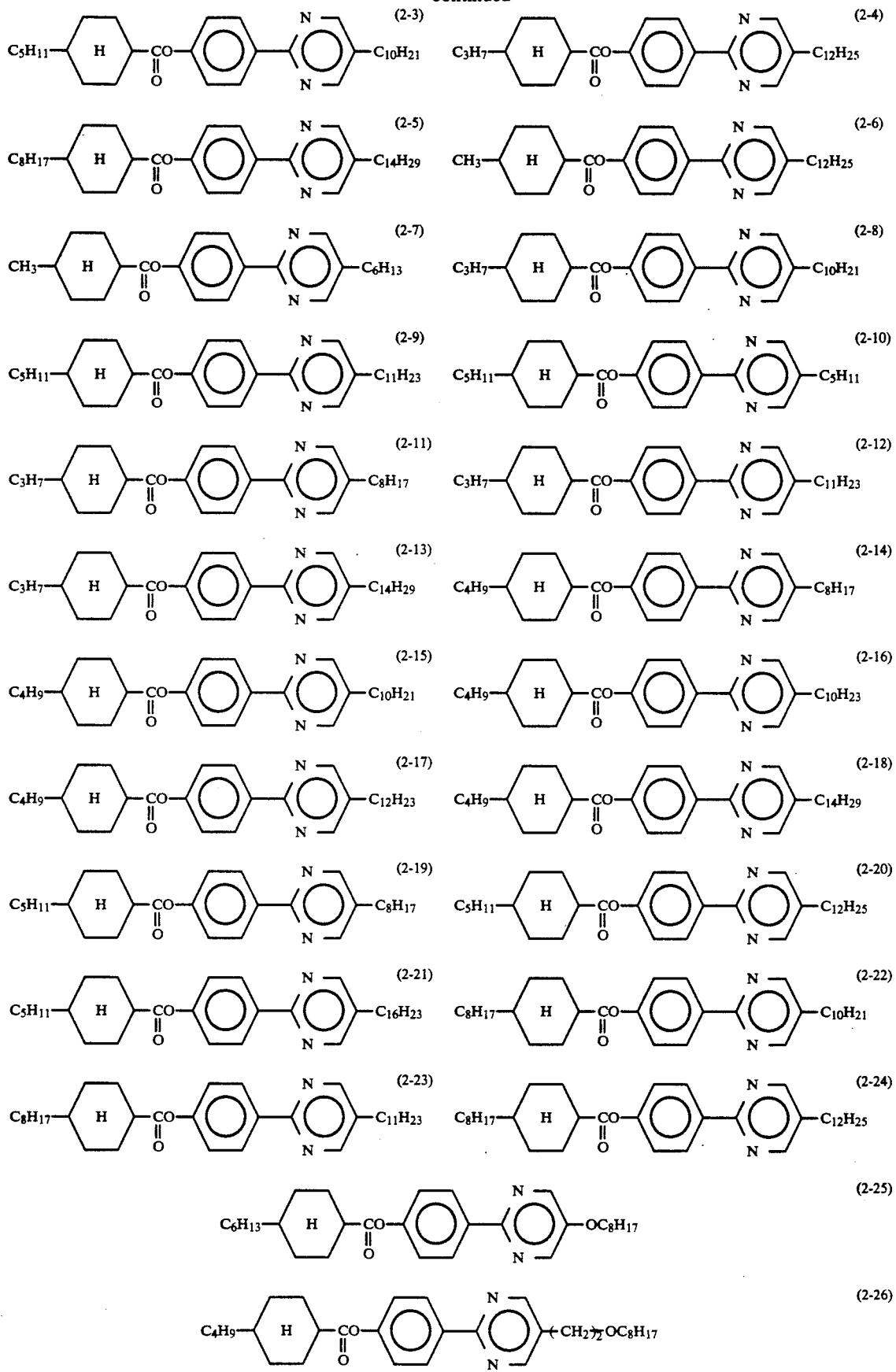

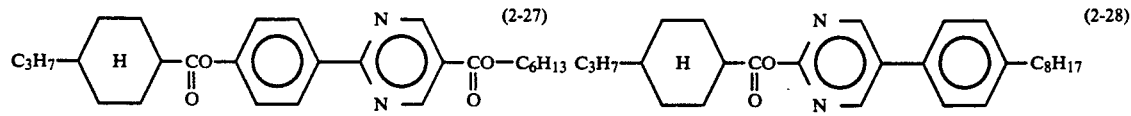
(2-27) (2-28)
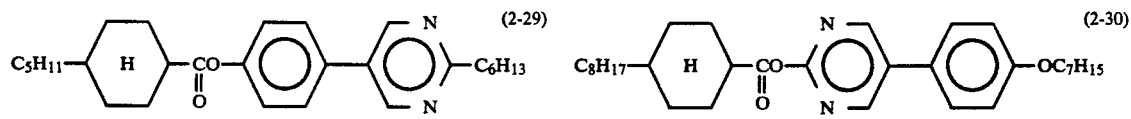
(2-29) (2-30)
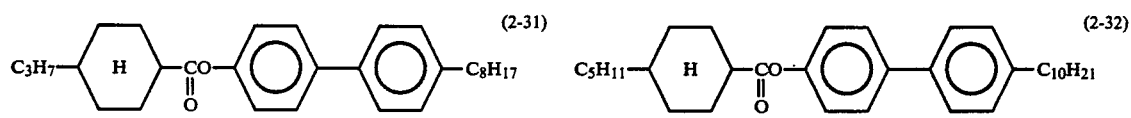
(2-31) (2-32)
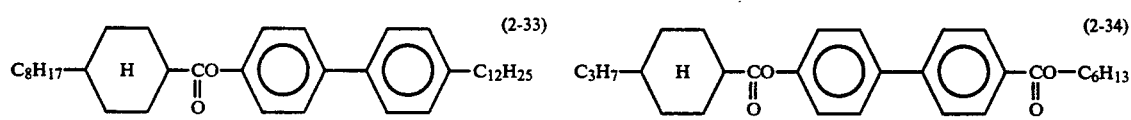
(2-33) (2-34)
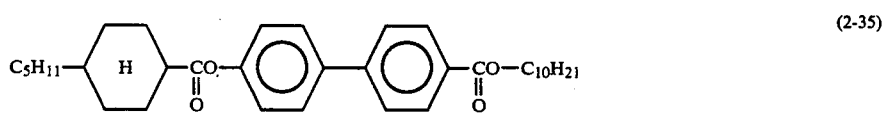
(2-35)
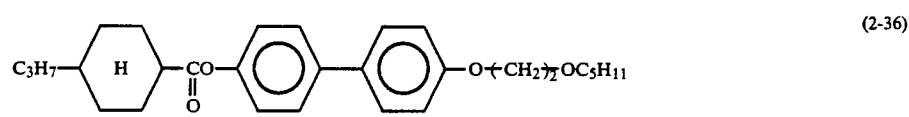
(2-36)
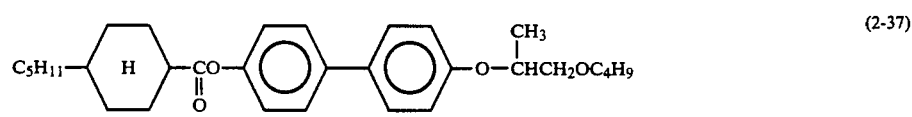
(2-37)
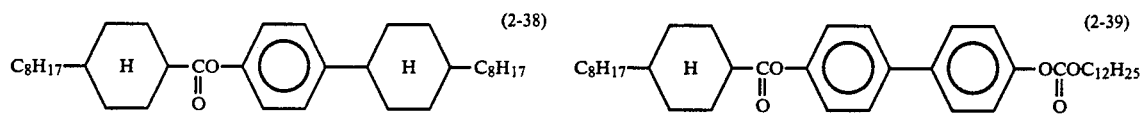
(2-38) (2-39)
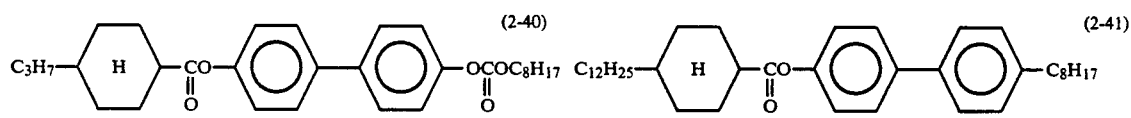
(2-40) (2-41)
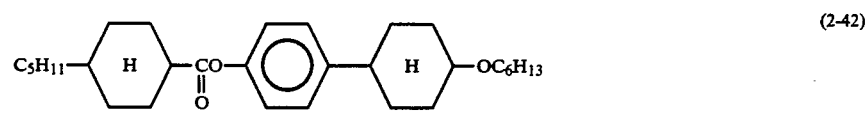
(2-42)
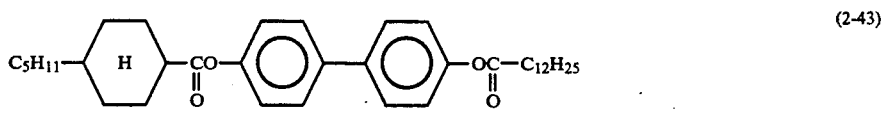
(2-43)
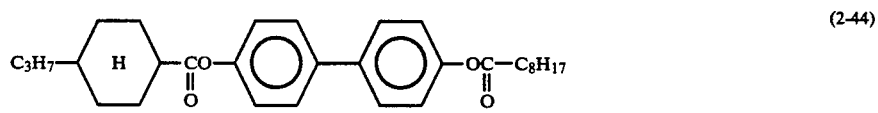
(2-44)
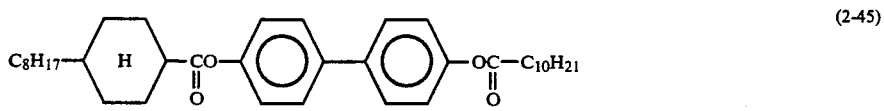
(2-45)

-continued $C_8H_{17}-\text{H}-\underset{O}{\overset{\|}{C}}O-\phenyl-\phenyl-O-\underset{O}{\overset{\|}{C}}-\underset{\text{CH}_3}{\overset{|}{C}}HC_2H_5$ (2-46)

$C_5H_{11}-\text{H}-\underset{O}{\overset{\|}{C}}O-\phenyl-\text{H}-C_{10}H_{21}$ (2-47)

$C_8H_{17}-\text{H}-\underset{O}{\overset{\|}{C}}O-\phenyl-\phenyl-O-\underset{O}{\overset{\|}{C}}-\underset{\text{Cl}}{\overset{|}{C}}HC_2H_5$ (2-48)

$C_5H_{11}-\text{H}-\underset{O}{\overset{\|}{C}}O-\text{H}-\phenyl-C_8H_{17}$ (2-49)

$C_3H_7-\text{H}-\underset{O}{\overset{\|}{C}}O-\phenyl-\phenyl-\underset{O}{\overset{\|}{C}}O-\underset{*}{\overset{\text{CH}_3}{\overset{|}{C}H}}-C_6H_{13}$ (2-50)

$C_5H_{11}-\text{H}-\underset{O}{\overset{\|}{C}}O-\phenyl-\phenyl-(CH_2)_3-\underset{*}{\overset{\text{CH}_3}{\overset{|}{C}H}}-C_2H_5$ (2-51)

$C_8H_{17}-\text{H}-\underset{O}{\overset{\|}{C}}O-\phenyl-\phenyl-O-CH_2\underset{*}{\overset{\text{CH}_3}{\overset{|}{C}H}}-C_2H_5$ (2-52)

$C_3H_7-\text{H}-\underset{O}{\overset{\|}{C}}O-\phenyl-\phenyl-O-(CH_2)_3-\underset{*}{\overset{\text{CH}_3}{\overset{|}{C}H}}OC_3H_7$ (2-53)

$C_8H_{17}-\text{H}-\underset{O}{\overset{\|}{C}}O-\phenyl-\phenyl-O-(CH_2)_4-\underset{*}{\overset{\text{CH}_3}{\overset{|}{C}H}}OCH_3$ (2-54)

$C_4H_9-\text{H}-\underset{O}{\overset{\|}{C}}O-\phenyl-\phenyl-O-(CH_2)_4-\underset{*}{\overset{\text{CH}_3}{\overset{|}{C}H}}OCH_3$ (2-55)

$C_3H_7-\text{H}-\underset{O}{\overset{\|}{C}}O-\phenyl-\phenyl-O-\underset{O}{\overset{\|}{C}}-(CH_2)_2-\underset{*}{\overset{\text{CH}_3}{\overset{|}{C}H}}OC_3H_7$ (2-56)

$C_5H_{11}-\text{H}-\underset{O}{\overset{\|}{C}}O-\phenyl-\phenyl-\underset{*}{\overset{\text{CH}_3}{\overset{|}{O}CH}}-CO-C_2H_5$ (2-57)

$C_3H_7-\text{H}-\underset{O}{\overset{\|}{C}}O-\phenyl-\phenyl-OCH_2\underset{*}{\overset{\text{Cl}}{\overset{|}{C}H}}-C_2H_5$ (2-58)

$C_3H_7-\text{H}-\underset{O}{\overset{\|}{C}}O-\phenyl-\phenyl-OCH_2\underset{*}{\overset{\text{F}}{\overset{|}{C}H}}C_5H_{11}$ (2-59)

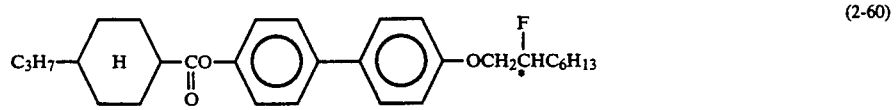
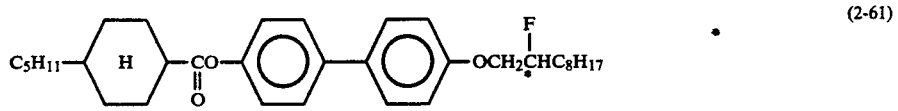
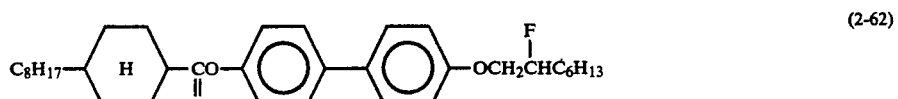
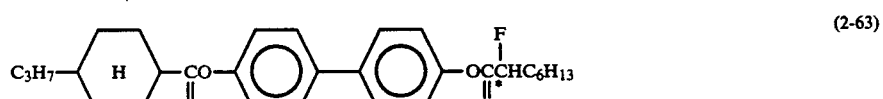
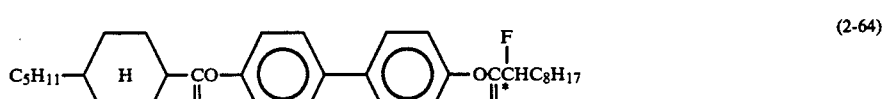
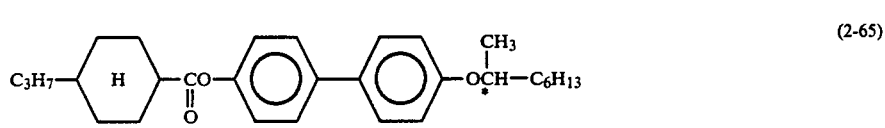
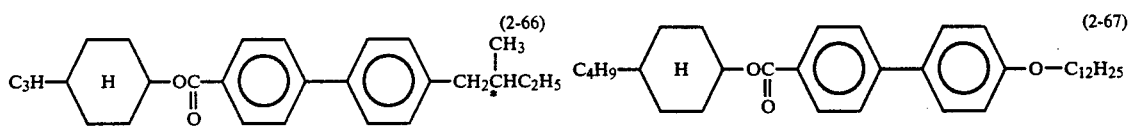
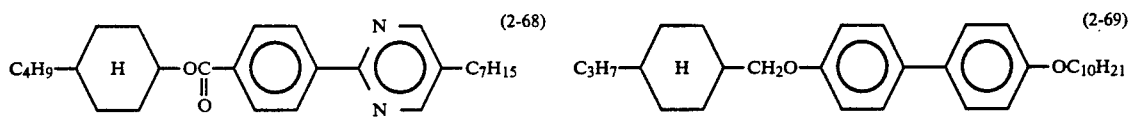
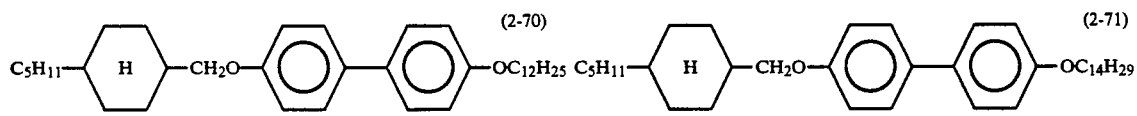
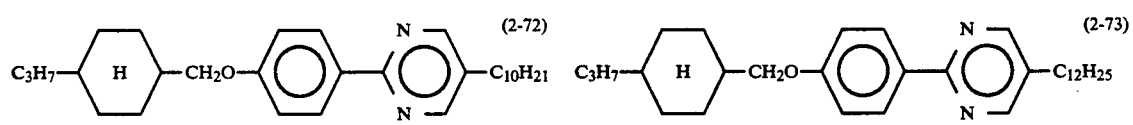
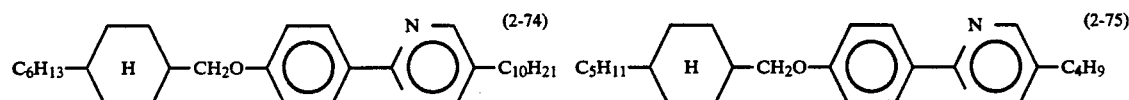
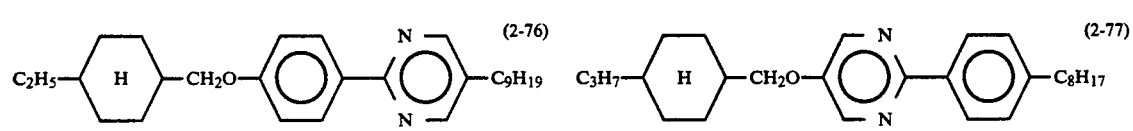
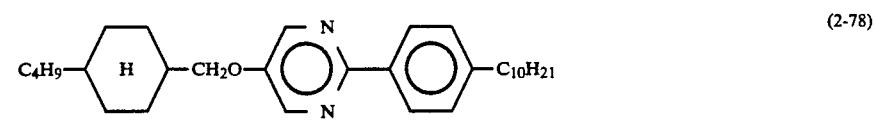

-continued
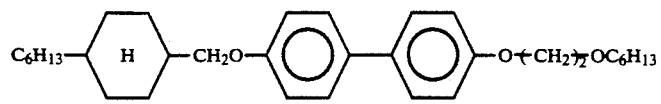 (2-79)
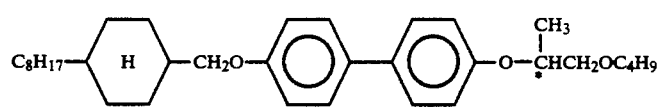 (2-80)
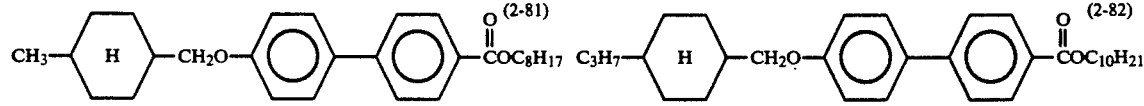 (2-81) (2-82)
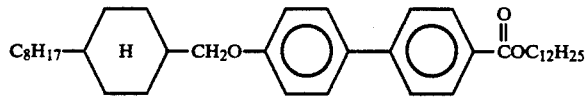 (2-83)
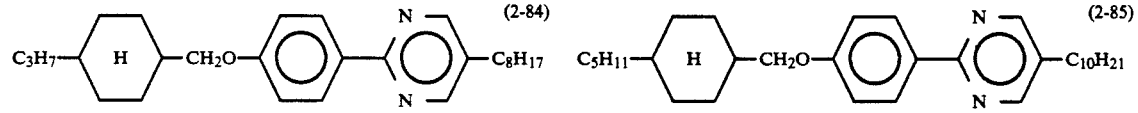 (2-84) (2-85)
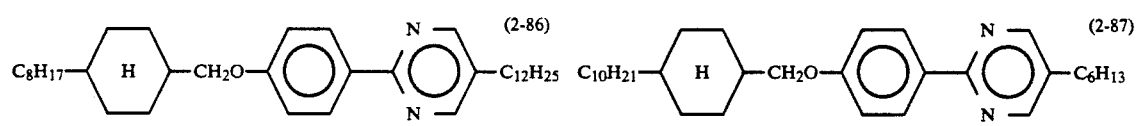 (2-86) (2-87)
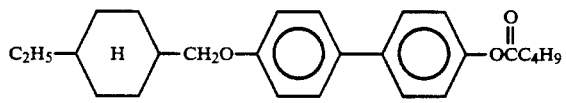 (2-88)
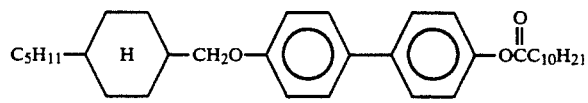 (2-89)
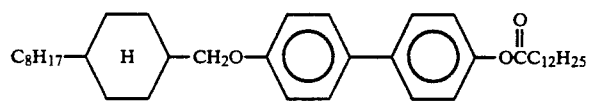 (2-90)
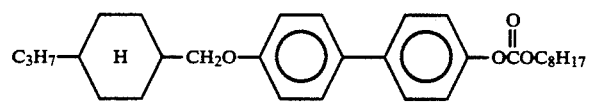 (2-91)
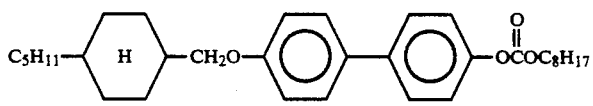 (2-92)
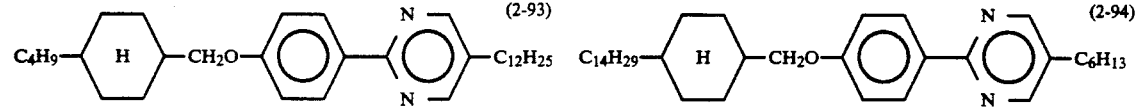 (2-93) (2-94)
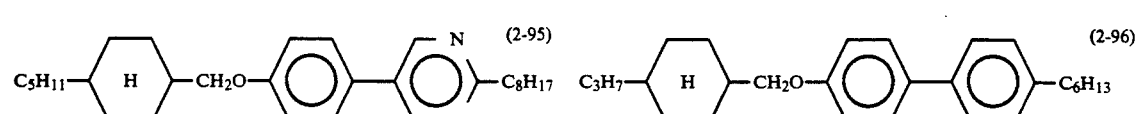 (2-95) (2-96)

-continued
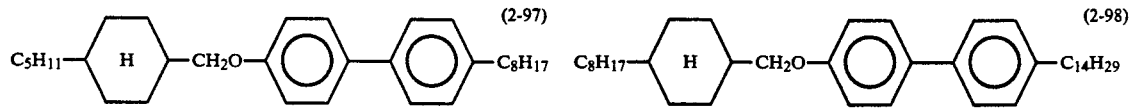 (2-97)
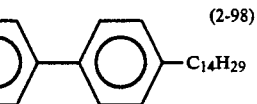 (2-98)
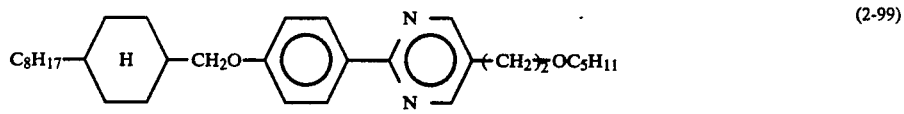 (2-99)
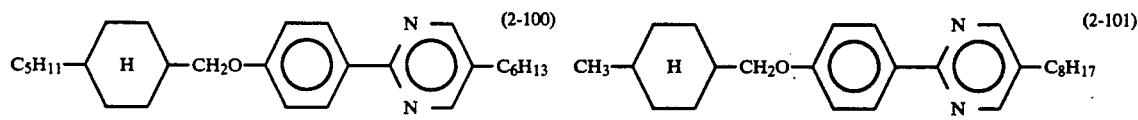 (2-100)
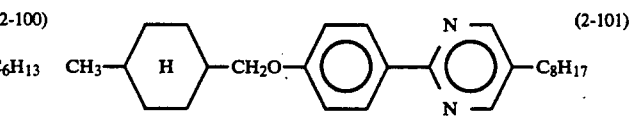 (2-101)
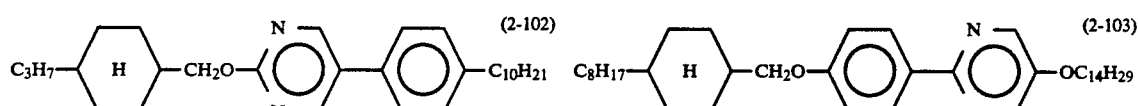 (2-102)
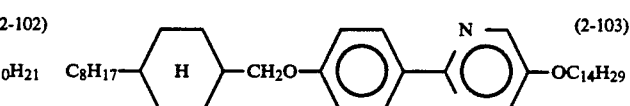 (2-103)
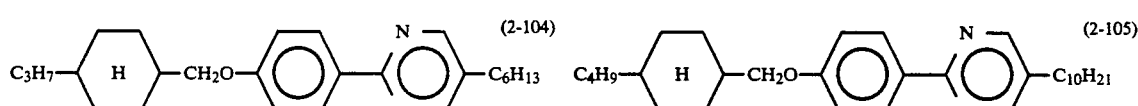 (2-104)
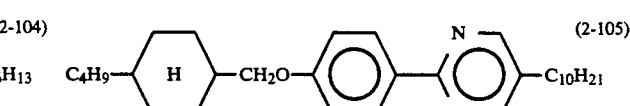 (2-105)
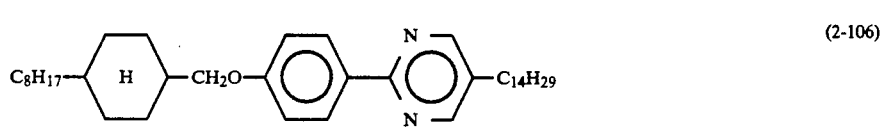 (2-106)
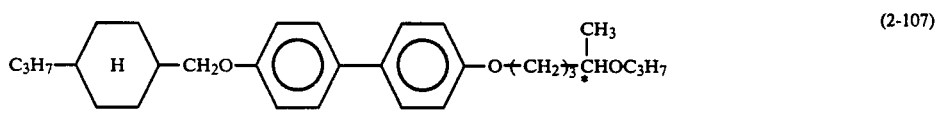 (2-107)
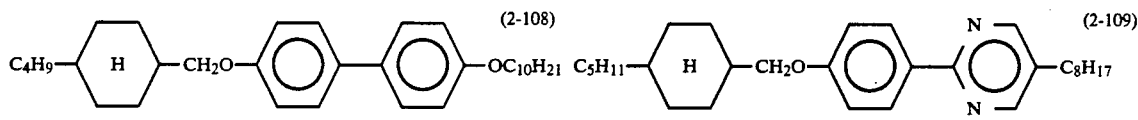 (2-108)
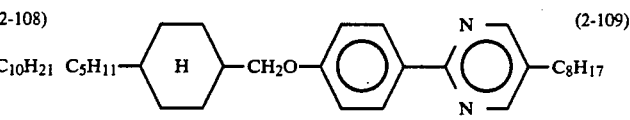 (2-109)
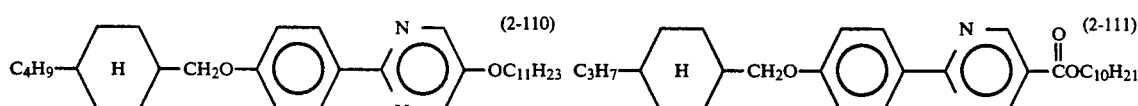 (2-110)
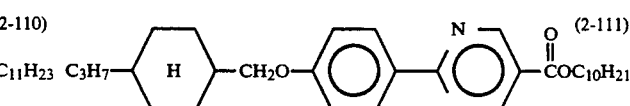 (2-111)
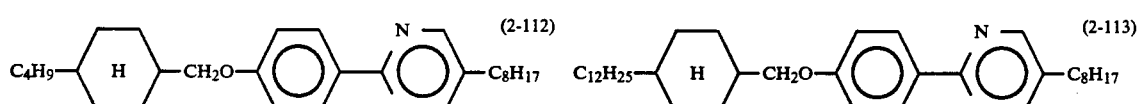 (2-112)
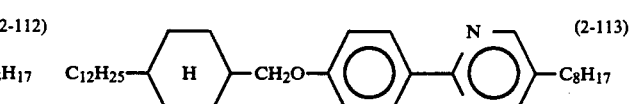 (2-113)
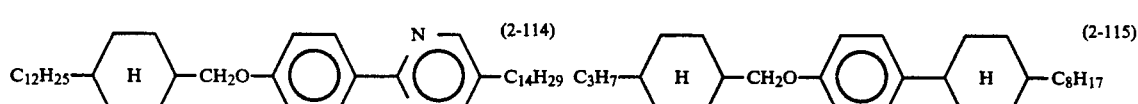 (2-114)
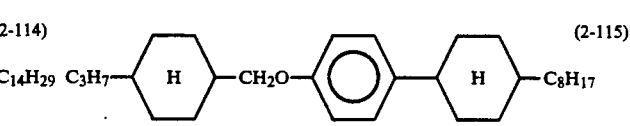 (2-115)
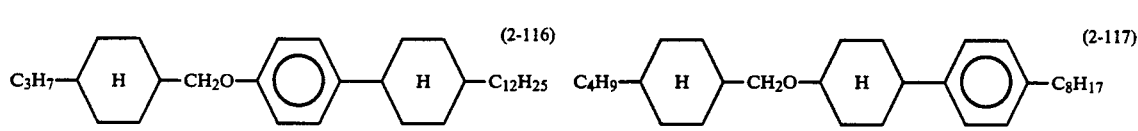 (2-116)
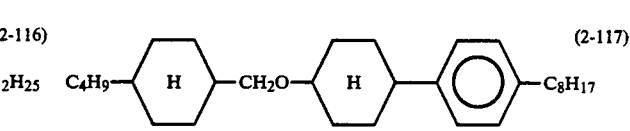 (2-117)
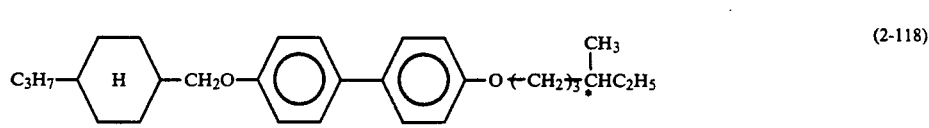 (2-118)

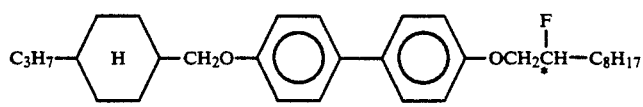
(2-119)

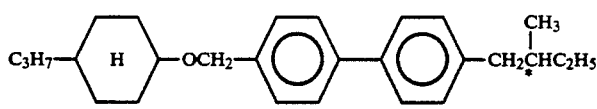
(2-120)

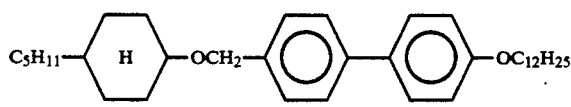
(2-121)

Representative examples of synthesis of compounds represented by the formula (II) are described below.

SYNTHESIS EXAMPLE 2

Synthesis of Compound Example No. 2-4

1.0 g (2.94 mmol) of 5-dodecyl-2-(4'-hydroxyphenyl)-pyrimidine was dissolved in respectively 4 ml of toluene and pyridine. A solution of 0.55 g of trans-4-n-propylcyclohexanecarbonyl chloride (manufactured by Kanto Kagaku K.K.) in 4 ml of toluene was gradually added dropwise thereto below 5° C. on an iced water bath. After the addition, the mixture was stirred for 12 hours at room temperature, and the reaction mixture was poured into 100 ml of iced water, followed by acidification with 6N-hydrochloric acid and extraction with benzene. The extracted solution was successively washed with water, 5%-solution hydrogen carbonate aqueous solution and water, followed by drying with magnesium sulfate and distilling-off of the solvent, to obtain a cream-colored crude product. The crude product was purified by column chromatography and recrystallized from ethanol/ethyl acetate mixture solvent to obtain 0.94 g of objective compound. Yield: 64.8%.

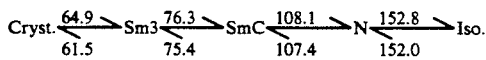

SYNTHESIS EXAMPLE 3

Synthesis of Compound Example No. 2-72

(1) A small amount of triethylamine was added to 10 g (53.6 mmol) of trans-4-n-propylcyclohexanecarbonyl chloride dissolved in 30 ml of ethanol, followed by 10 hours of stirring at room temperature. The reaction mixture was poured into 100 ml of iced water, acidified with 6N-hydrochloric acid and extracted with isopropyl ether. The organic layer was repeatedly washed with water until the aqueous layer became a neutral, followed by drying with magnesium sulfate, distilling-off of the solvent and purification by silica gel column chromatography to obtain 9.9 g of ethyl trans-4-n-propylcyclohexylcarboxylate.

(2) 0.73 g (19.1 mmol) of lithium aluminum hydride was added to 30 ml of dry ether, heat-refluxed for 1 hour and cooled to 10° C. on an iced water bath, and a solution of 5 g (25.5 mmol) of ethyl trans-4-n-propylcyclohexylcarboxylate in 30 ml of dry ether was gradually added dropwise thereto. After the addition, the mixture was stirred for 1 hour and further heat-refluxed for 1 hour, followed by treatment with ethyl acetate and with 6N-hydrochloric acid and pouring into 200 ml of iced water. The resultant mixture was extracted with isopropyl ether and the organic layer was successively washed with water, sodium hydroxide aqueous solution and water, followed by drying with magnesium sulfate, distilling-off of the solvent and purification by silica gel column chromatography to obtain 3.5 g of trans-4-n-propylcyclohexylmethanol.

(3) 3.4 g (22.4 mmol) of trans-4-n-propylcyclohexylmethanol was dissolved in 20 ml of pyridine. A solution of 5.3 g of p-toluenesulfonyl chloride in 20 ml of pyridine was added dropwise thereto below 5° C. on an iced water bath under cooling, followed by 10 hours of stirring at room temperature and pouring into 200 ml of iced water. The resultant mixture was acidified with 6N-hydrochloric acid and extracted with isopropyl ether. The organic layer was repeatedly washed with water until the aqueous layer became neutral, followed by drying with magnesium sulfate and distilling-off of the solvent, to obtain trans-4-n-propylcyclohexylmethyl-p-toluenesulfonate.

(4) 6.3 g (20.2 mmol) of 5-decyl-2-(4'-hydroxyphenyl)pyrimidine was dissolved in 40 ml of dimethylformamide, 1.5 g of potassium hydroxide (85%) was added thereto, followed by 1 hour of stirring at 100° C., 6.9 g of trans-4-n-propylcyclohexylmethyl-p-toluenesulfonate was added thereto, followed further by 4 hour of stirring at 100 C. After the reaction, the reaction mixture was poured into 200 ml of iced water and extracted with benzene. The organic layer was washed with water and dried with magnesium sulfate, followed by distilling-off of the solvent, purification by silica gel column chromatography and recrystallization from ethanol/ethyl acetate mixture solvent to obtain the above compound Example No. 2-72.

IR (cm$^{-1}$): 2920, 2840, 1608, 1584, 1428, 1258, 1164, 800

Phase transition temperature (°C.)

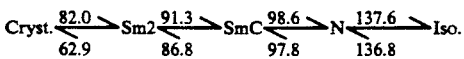

Sm2: smectic phase other than SmA and SmC (unidentified)

In a preferred embodiment, the ferroelectric chiral smectic liquid crystal composition according to the present invention further comprises a mesomorphic compound having a negative dielectric anisotropy, which is preferably selected from those represented by the following formulas (III-1) to (III-5): Formula (III-1):

Formula (III-1):

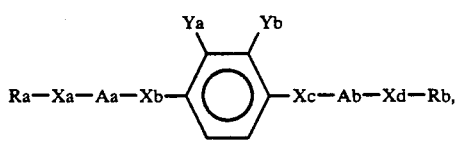

wherein Ra and Rb respectively denote a linear or branched alkyl group capable of having a substituent; Xa and Xd respectively denote a single bond, —O—, —CO—, or —OC—; Xb and Xc respectively
         ‖           ‖
         O           O denote a single bond, —CO—, —OC— or
                        ‖       ‖
                        O       O —CH₂CH₂—; Aa and Ab respectively denote a single bond, 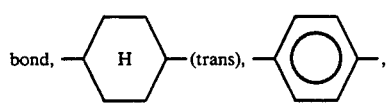

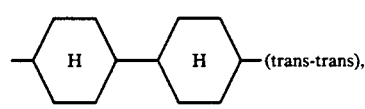

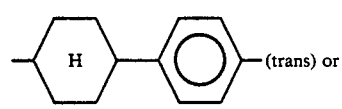

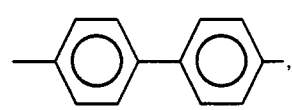

with proviso that when Aa and Ab are both single bonds, Xb and Xc are both single bonds, and Xa and Xd are both single bonds or —O—, or Xa is —CO— and Xd is —OC—;
      ‖              ‖
      O              O and Ya and Yb are respectively cyano group, halogen or hydrogen with proviso that Ya and Yb cannot be hydrogen simultaneously;

Formula (III-2):

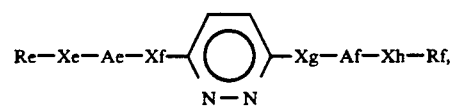

wherein Re and Rf respectively denote a linear or branched alkyl group capable of having a substituent; Xe and Xh are respectively a single bond, —O—, —CO— or —OC—; Xf and Xg are respectively
      ‖         ‖
      O         O —CO—, —OC— or a single bond; and Ae and Af are
 ‖     ‖
 O     O respectively 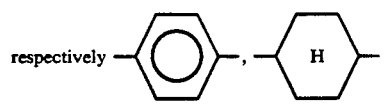

or a single bond with proviso that Ae and Af cannot be a single bond simultaneously;

Formula (III-3):

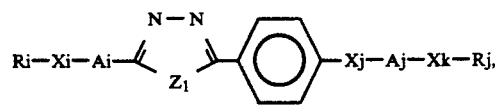

wherein Ai is a single bond or ⟨○⟩—;

Aj is a single bond, ⟨H⟩— or ⟨○⟩—;

Ri and Rj are respectively a linear or branched alkyl group capable of having a substituent with proviso that Ri and Rj are linear alkyl groups when Aj is a single bond; Z₁ is —O— or —S—; Xi and Xk are respectively a single bond, —O—, —CO—, —OC— or —OCO—;
      ‖      ‖       ‖
      O      O       O Xj is a single bond, —CO— —OC—,
                      ‖      ‖
                      O      O -CH₂O— or —OCH₂—with proviso that Xi is a single bond when Ai is a single bond, Xj is not a single bond when Aj is

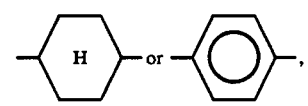

and Xk is a single bond when Aj is a single bond;

Formula (III-4):

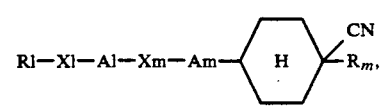

wherein Rl and Rm are respectively a linear or branched alkyl group capable of having a substituent; Al and Am are respectively a single bond,

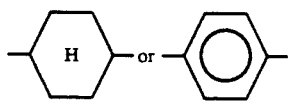

with proviso that Al and Am cannot be a single bond simultaneously; Xl is a single bond, —O—, —CO—, or —OC—; and Xm is a single bond,
        ‖              ‖
        O              O

—CO—, —OC—, —CH$_2$O—, —OCH$_2$—,
  ‖      ‖
  O      O

—CH$_2$CH$_2$— or —C≡C—;

Formula (III-5):

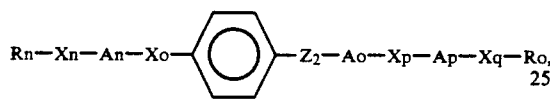

wherein Rn and Ro are respectively a linear or branched alkyl group capable of having a substituent; Xn and Xq are respectively a single bond, —O—, —CO— or —OC—; Xo and Xp are respectively
        ‖         ‖
        O         O a single bond, —CO—, —OC—, —CH$_2$O—,
                 ‖      ‖
                 O      O —OCH$_2$— or —CH$_2$CH$_2$—; An and Ap are respectively

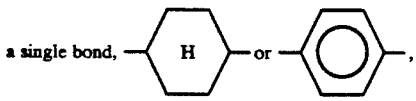

Ao is <image with phenyl or cyclohexyl>; and

Z$_2$ is —C=CH— or —CH—CH$_2$—.
         |            |
         CN           CN

In the above formulas (III-1) to (III-5), the alkyl groups Ra–Ro may respectively have 1–18 carbon atoms, preferably 4–16 carbon atoms, further preferably 6–12 carbon atoms.

Specific examples of mesomorphic compounds represented by the general formulas (III-1) to (III-5) may respectively include those denoted by the structural formulas shown below.

Formula (III-1)

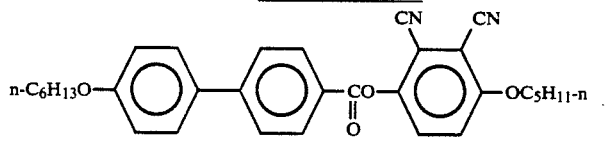
(3-1)

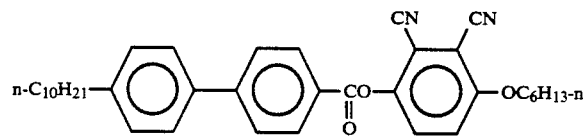
(3-2)

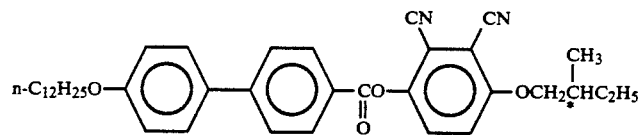
(3-3)

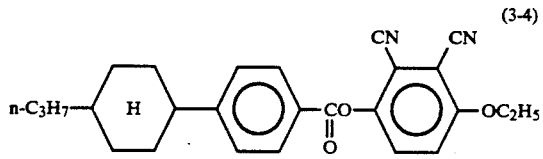
(3-4)

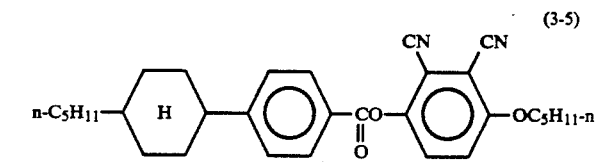
(3-5)

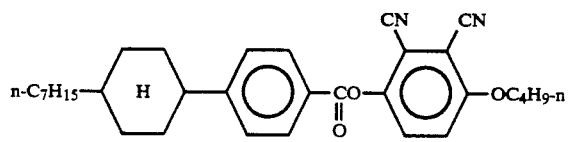
(3-6)

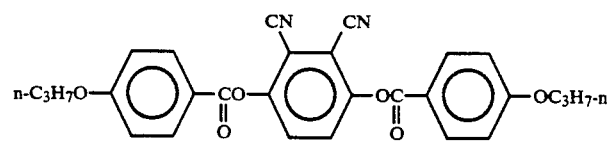
(3-7)

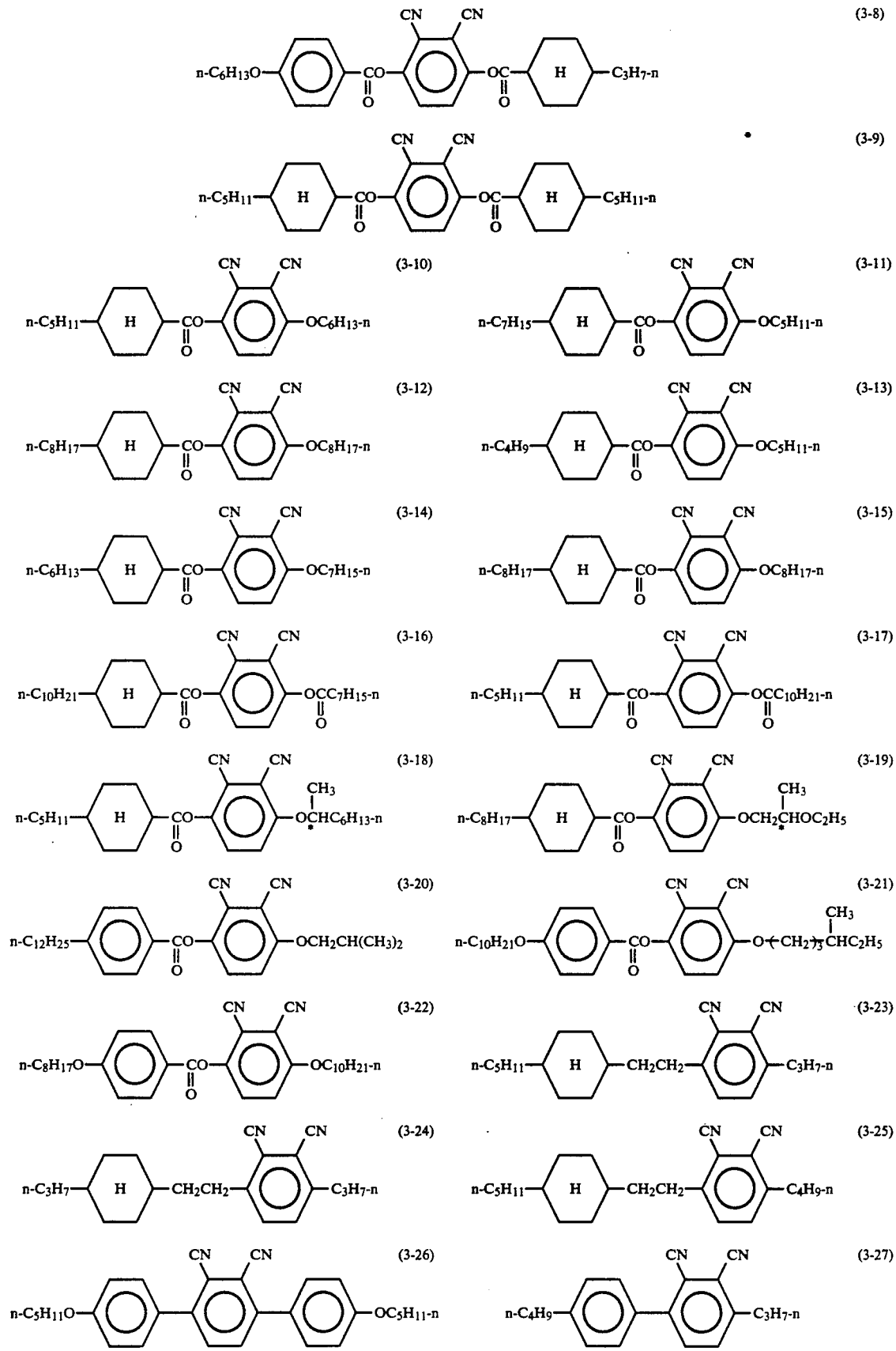

-continued
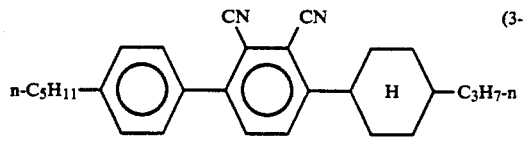 (3-28)
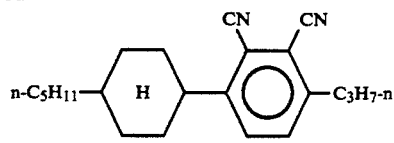 (3-29)
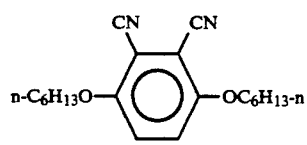 (3-30)
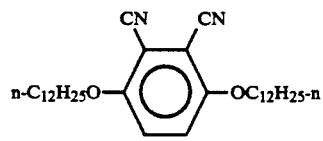 (3-31)
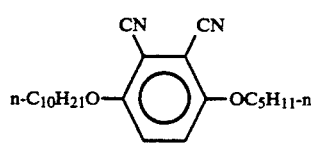 (3-32)
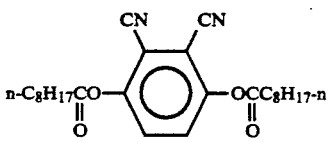 (3-33)
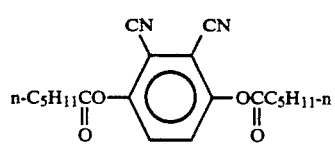 (3-34)
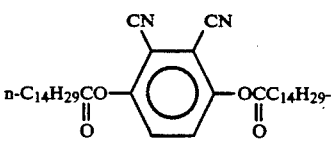 (3-35)
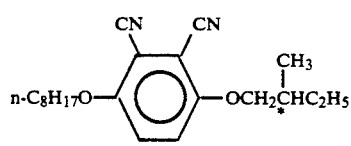 (3-36)
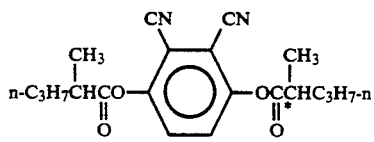 (3-37)
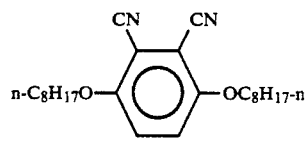 (3-38)
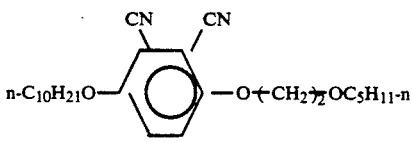 (3-39)
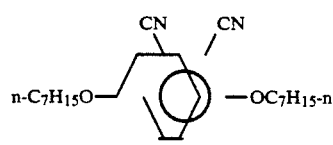 (3-40)
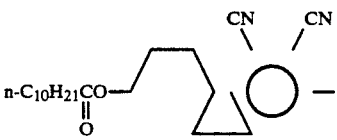 (3-41)
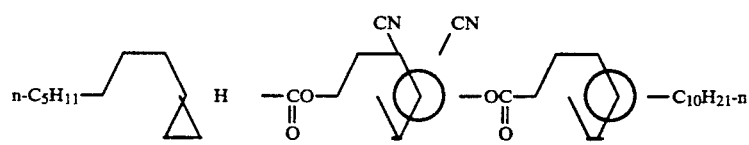 (3-42)
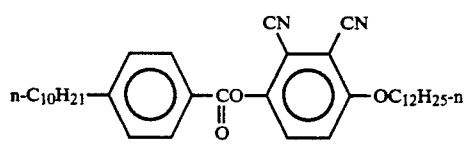 (3-43)
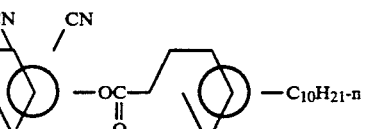 (3-44)
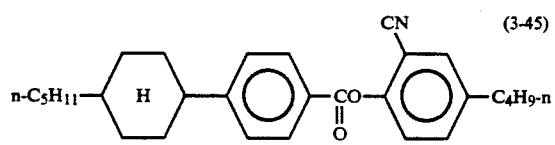 (3-45)
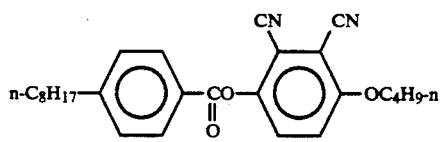 (3-46)
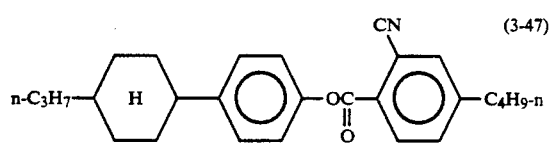 (3-47)
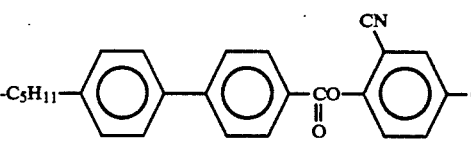 (3-48)

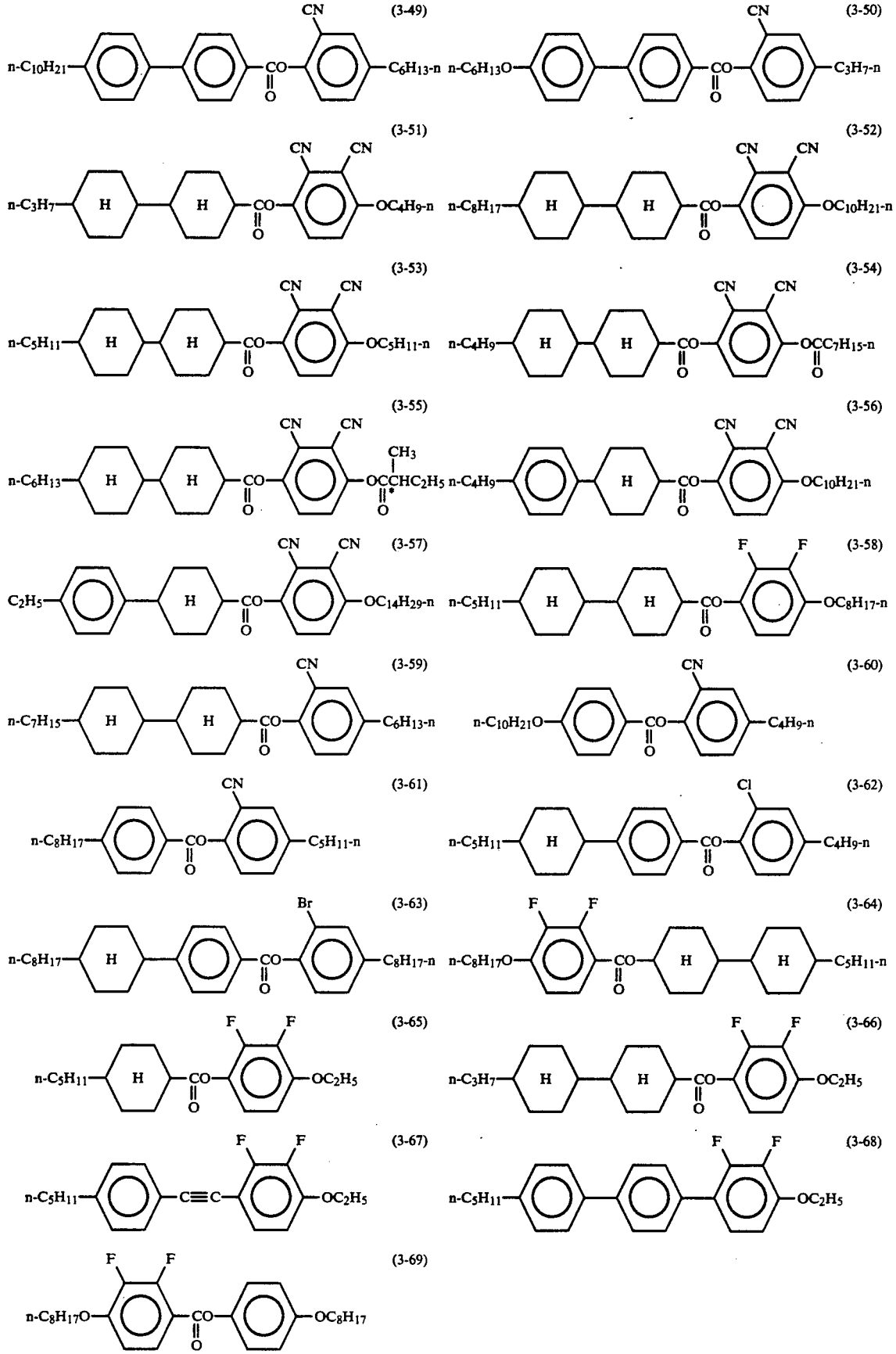

-continued
Formula (III-2)
(3-70) 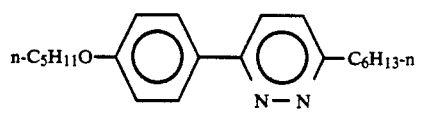
(3-71) 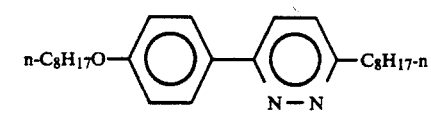
(3-72) 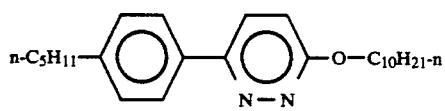
(3-73) 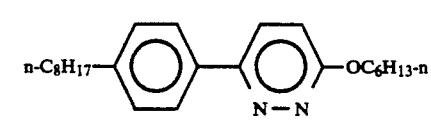
(3-74) 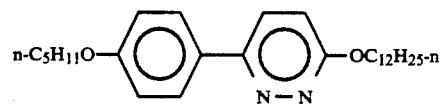
(3-75) 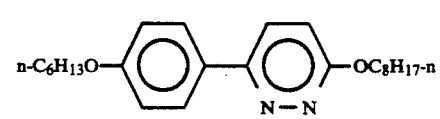
(3-76) 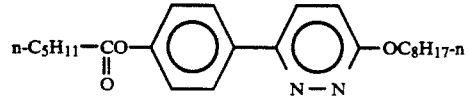
(3-77) 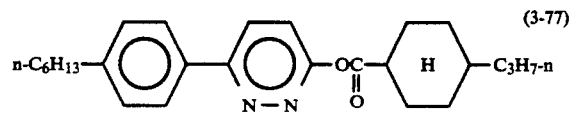
(3-78) 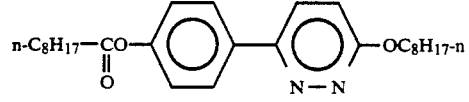
(3-79) 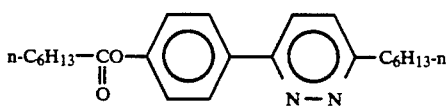
(3-80) 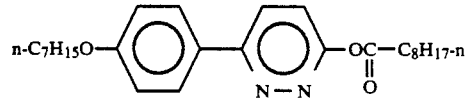
(3-81) 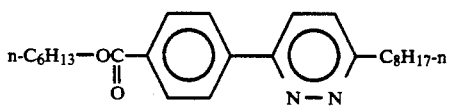
(3-82) 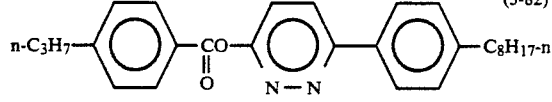
(3-83) 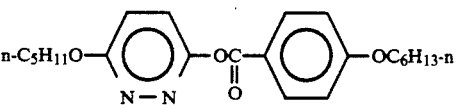
(3-84) 
(3-85) 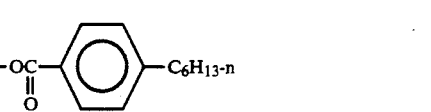
(3-86) 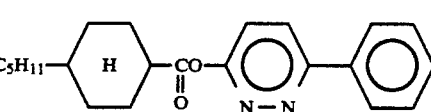
(3-87) 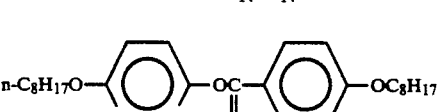
(3-88) 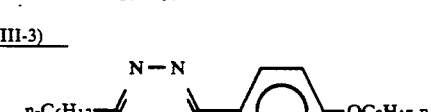
(3-89) 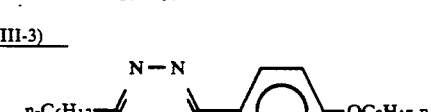
Formula (III-3)
(3-90) 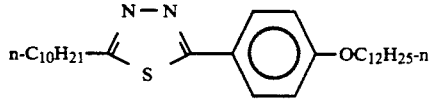
(3-91) 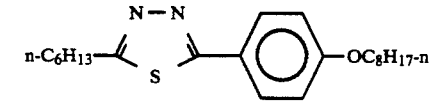
(3-92) 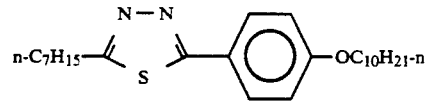
(3-93) 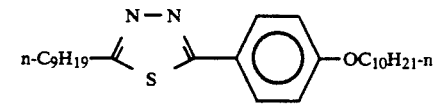

-continued
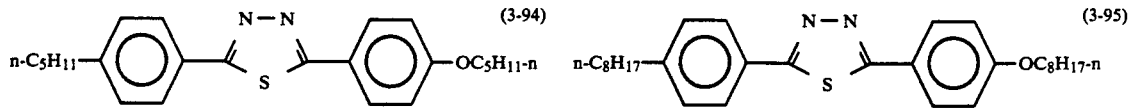  (3-94) (3-95)
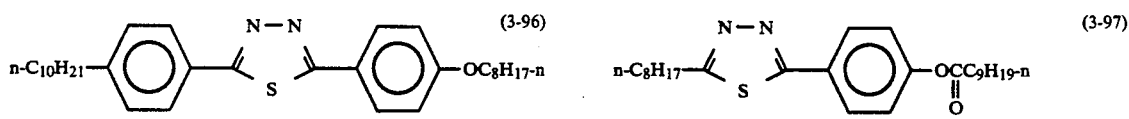  (3-96) (3-97)
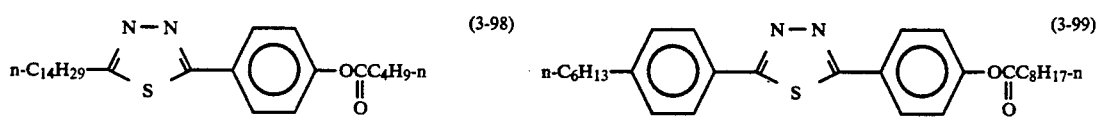  (3-98) (3-99)
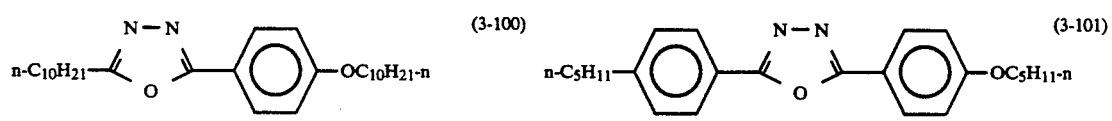  (3-100) (3-101)
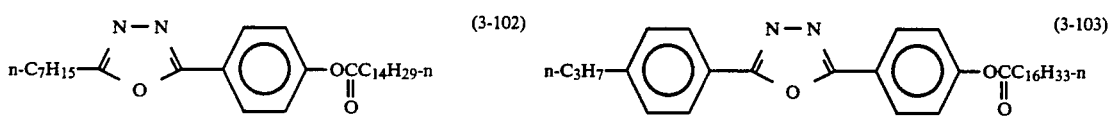  (3-102) (3-103)
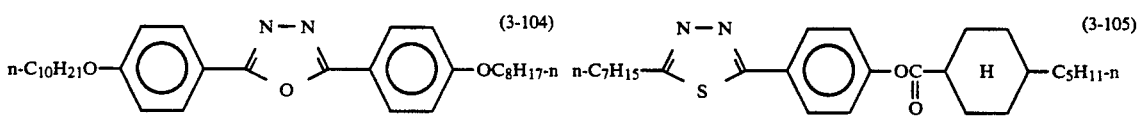  (3-104) (3-105)
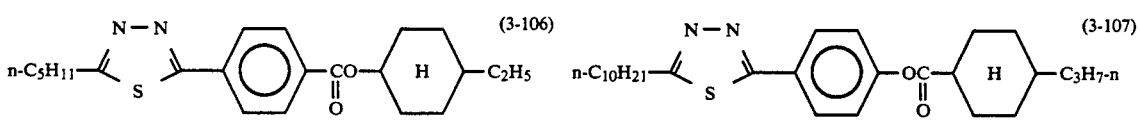  (3-106) (3-107)
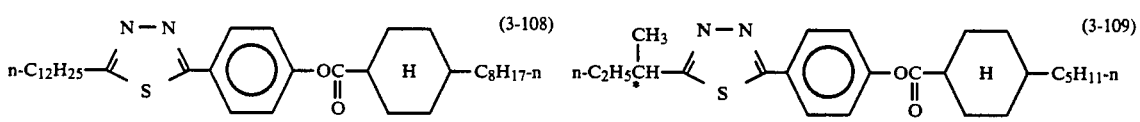  (3-108) (3-109)
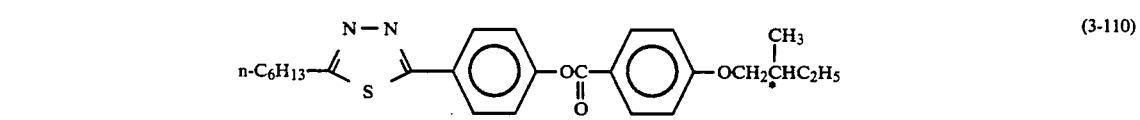  (3-110)
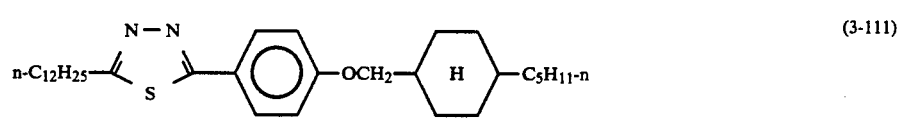  (3-111)
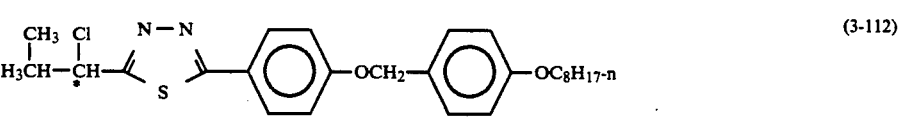  (3-112)
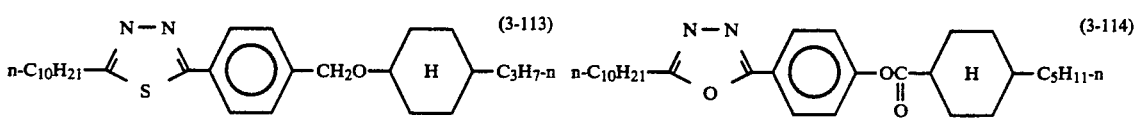  (3-113) (3-114)
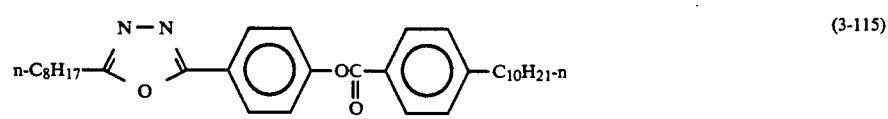  (3-115)

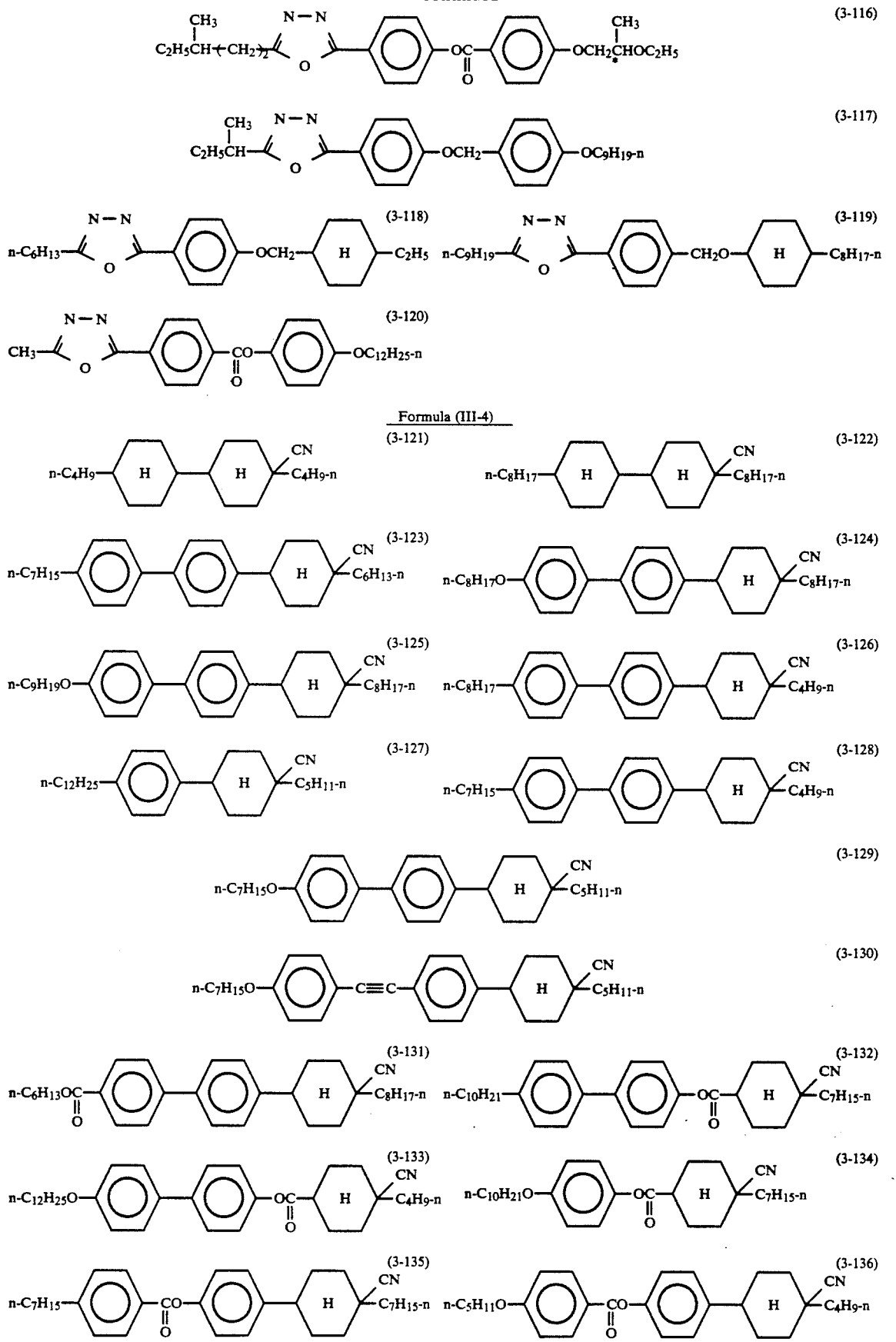

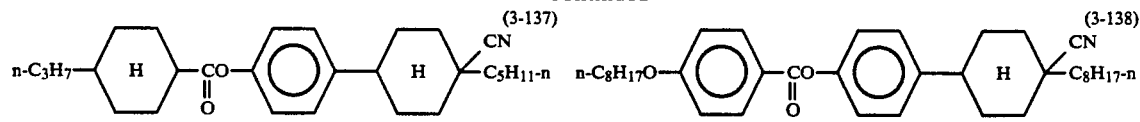 (3-137) (3-138)
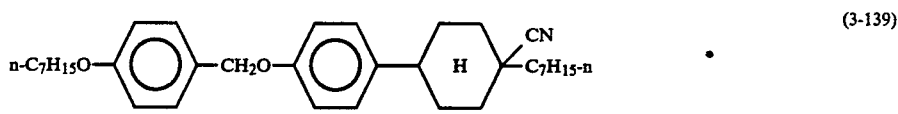 (3-139)
 (3-140)
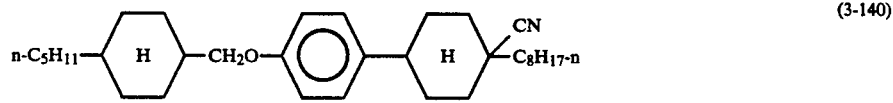 (3-141)
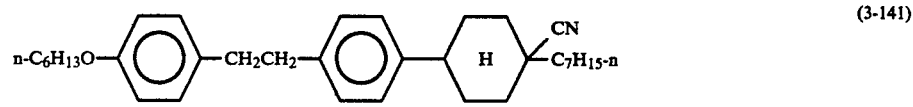 (3-142)
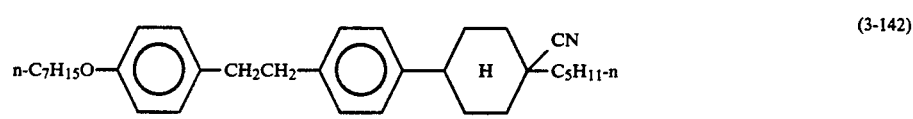 (3-143)
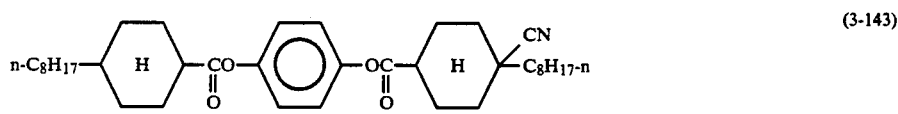 (3-144)
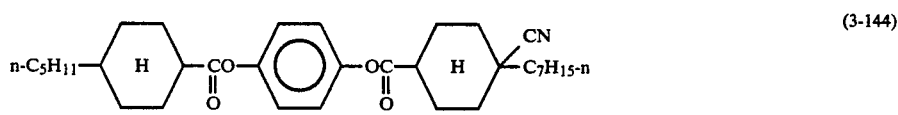 (3-145)
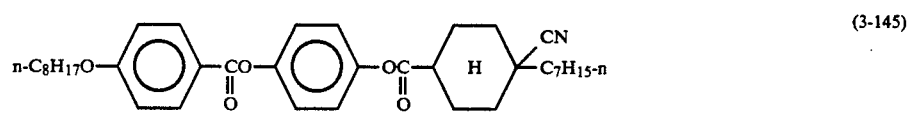 (3-146) (3-147)
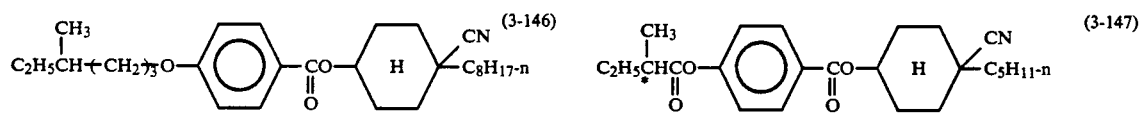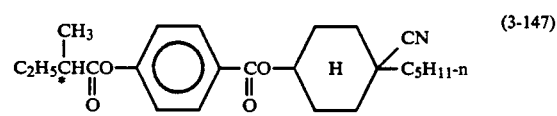 (3-148)
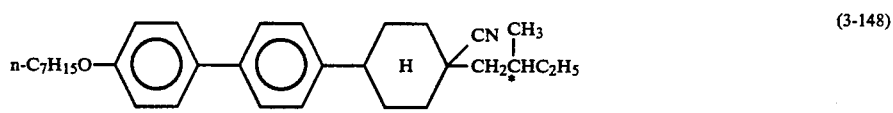 (3-149) (3-150)
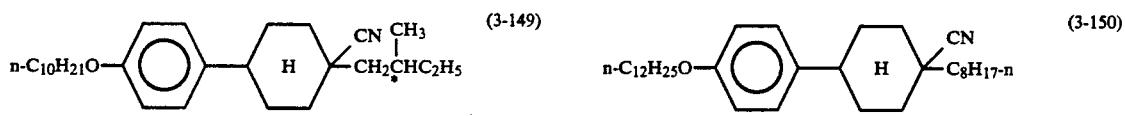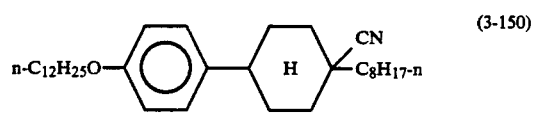 (3-151)
Formula (III-5)
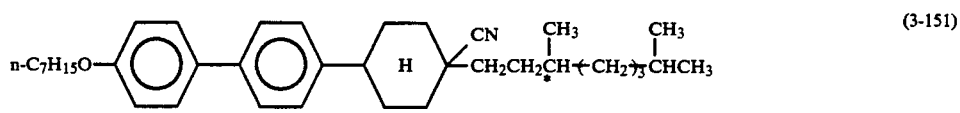 (3-152)
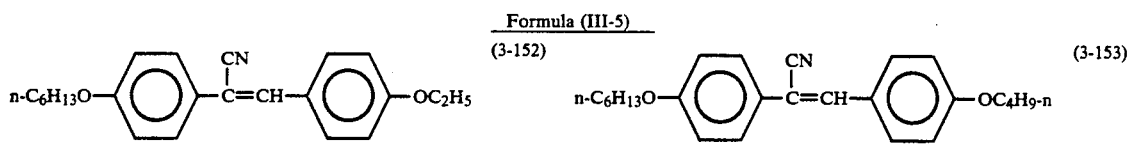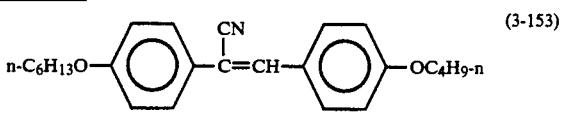 (3-153)

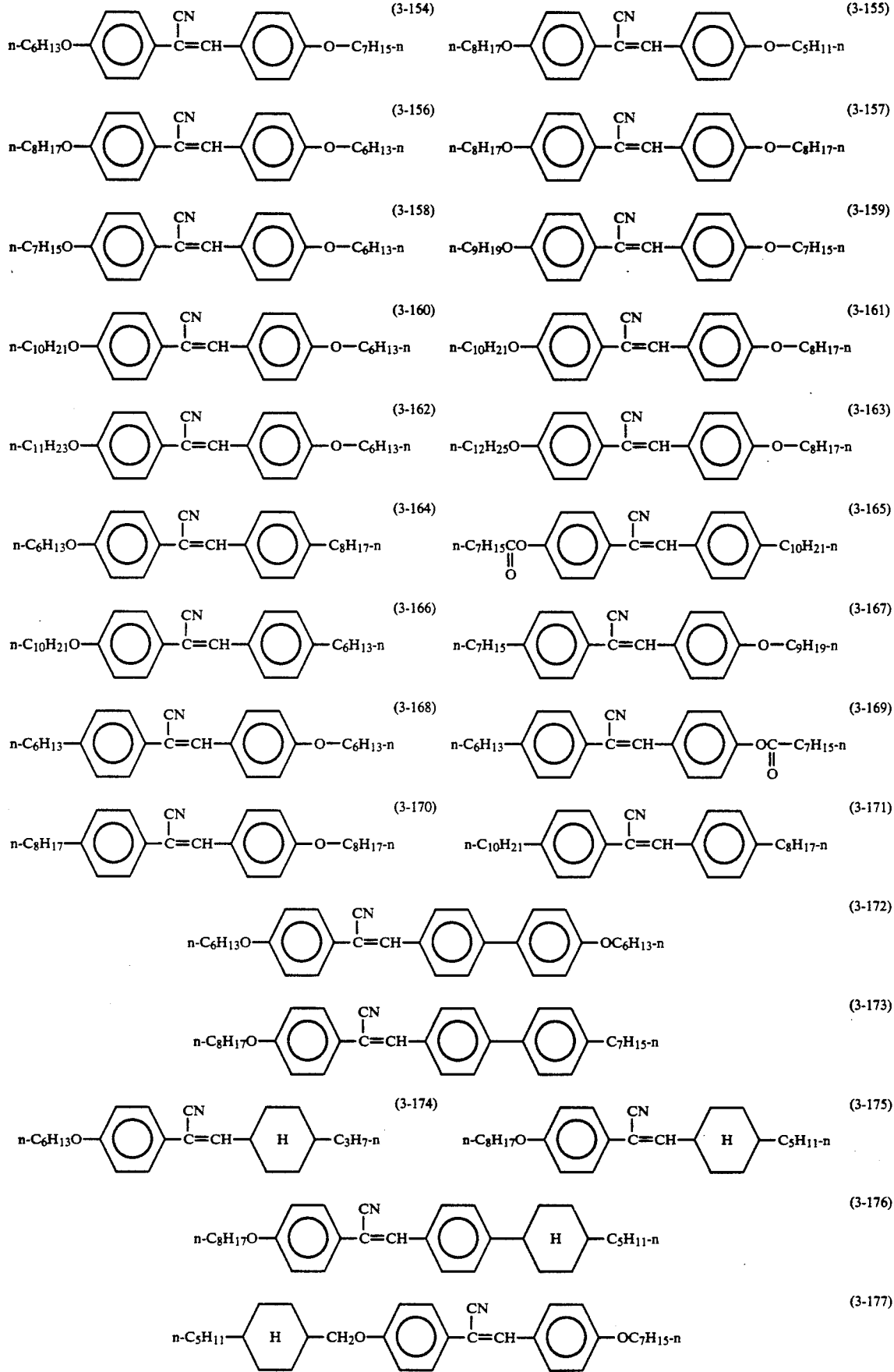

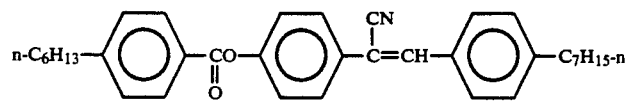 (3-178)

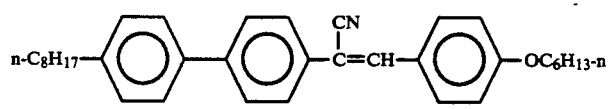 (3-179)

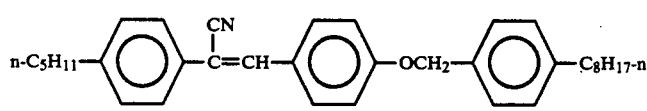 (3-180)

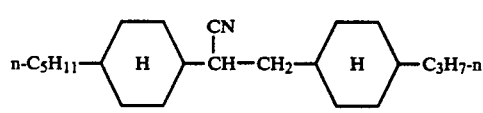 (3-181)

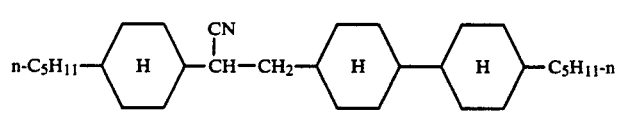 (3-182)

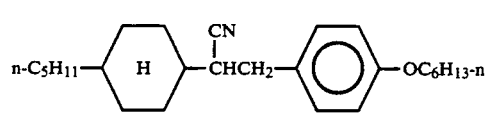 (3-183)

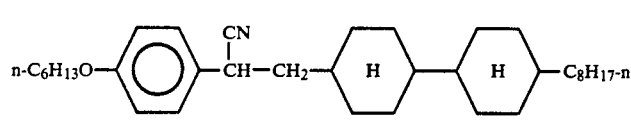 (3-184)

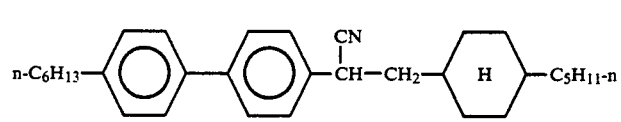 (3-185)

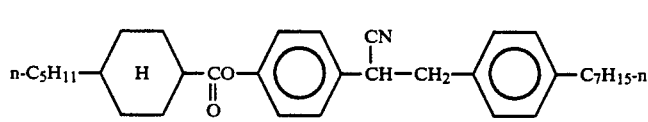 (3-186)

The mesomorphic compound having a negative dielectric anisotropy $\Delta\epsilon$ may preferably have $\Delta\epsilon < -2$, preferably $\Delta\epsilon < -5$, further preferably $\Delta\epsilon < -10$.

The liquid crystal composition according to the present invention may be obtained by mixing at least one species of the compound represented by the formula (I), at least one species of the compound represented by the formula (II), optionally at least one species of a mesomorphic compound having a negative dielectric anisotropy and another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structure formulas.

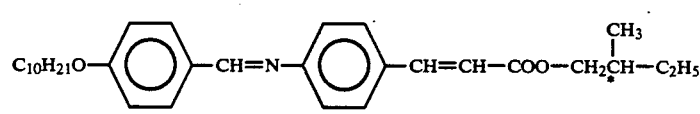 (1)

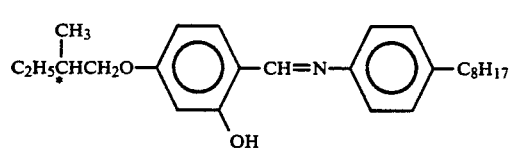 (2)

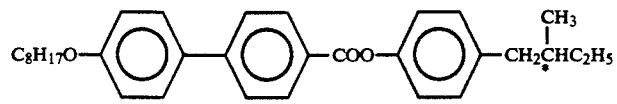 (3)
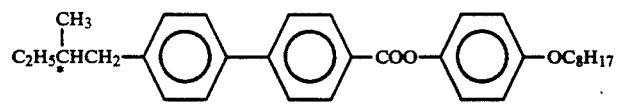 (4)
 (5)
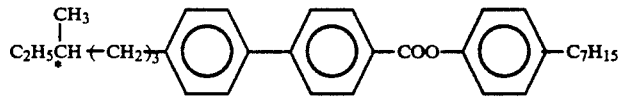 (6)
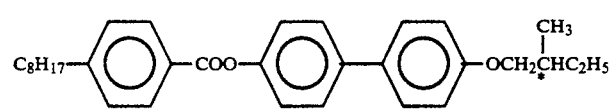 (7)
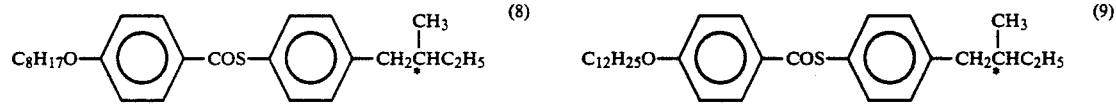 (8) (9)
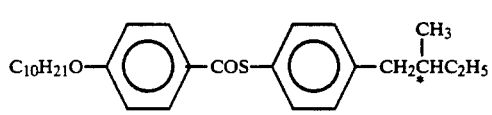 (10)
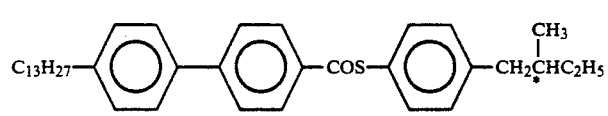 (11)
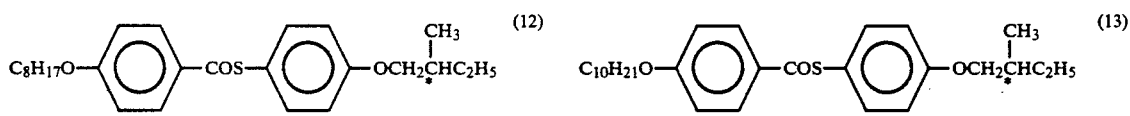 (12) (13)
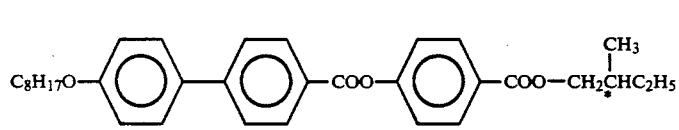 (14)
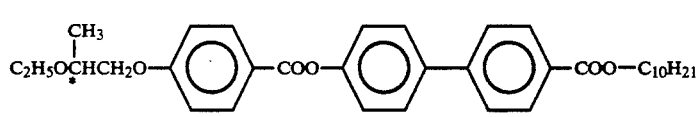 (15)
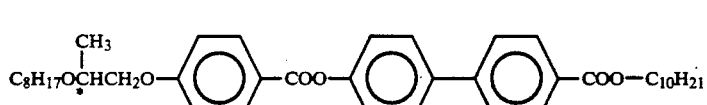 (16)
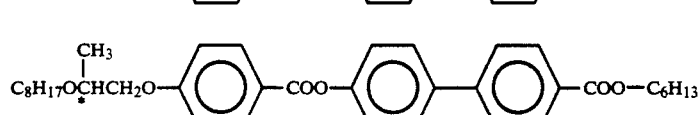 (17)
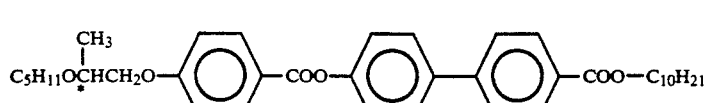 (18)

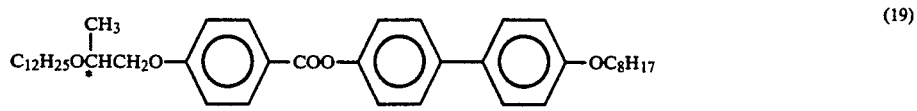
(19)
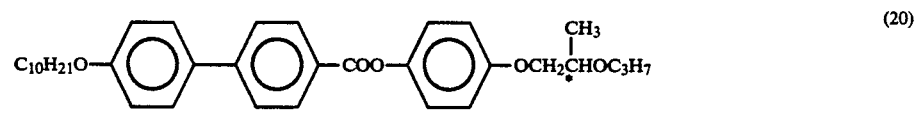
(20)
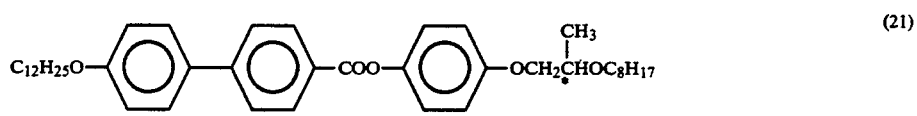
(21)
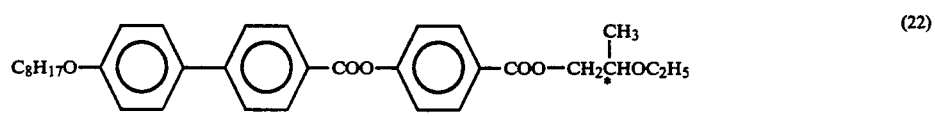
(22)
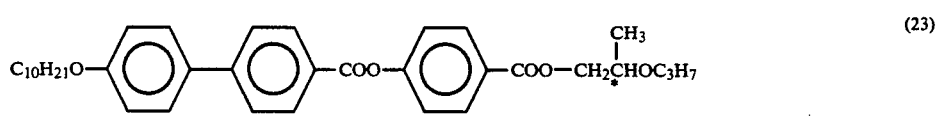
(23)
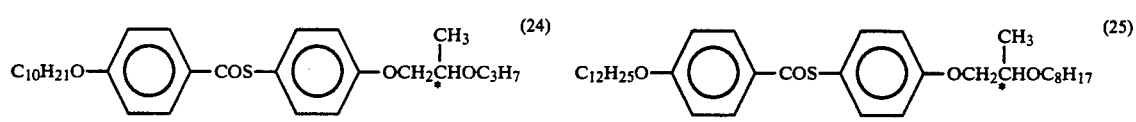
(24) (25)
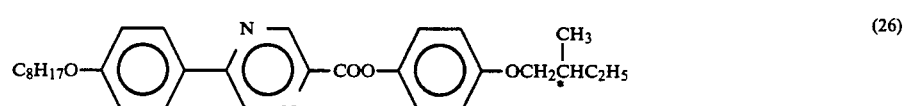
(26)
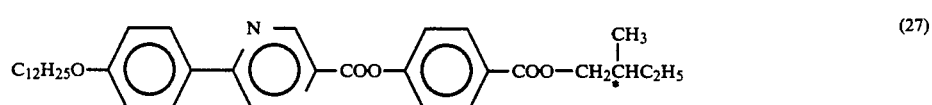
(27)
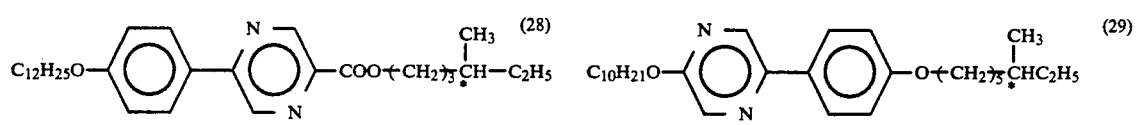
(28) (29)
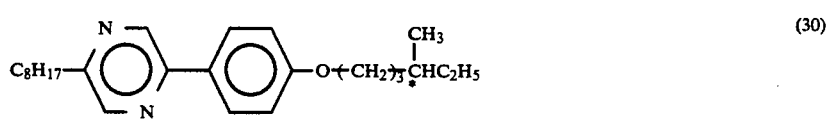
(30)
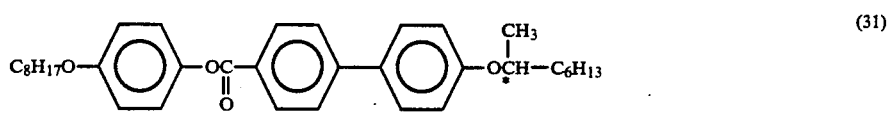
(31)
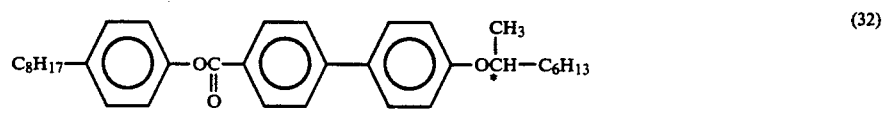
(32)
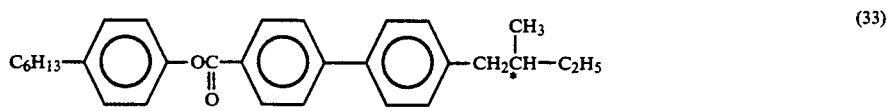
(33)

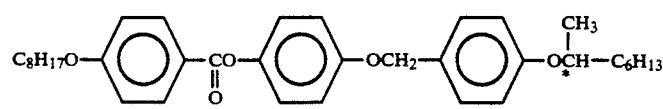
(34)
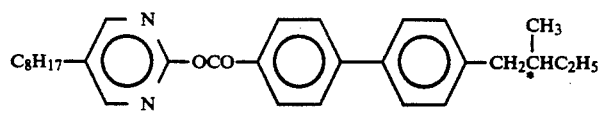
(35)
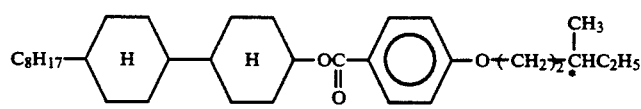
(36)
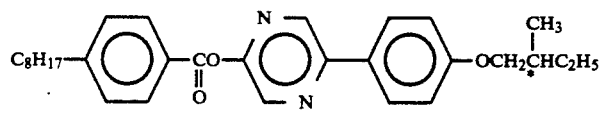
(37)
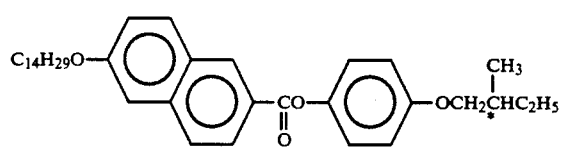
(38)
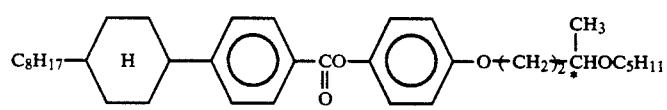
(39)
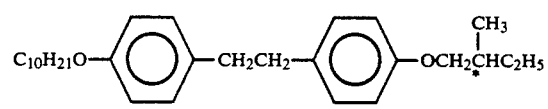
(40)
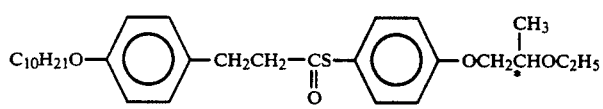
(41)
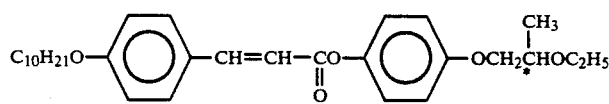
(42)
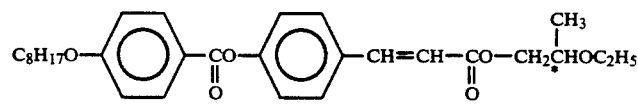
(43)
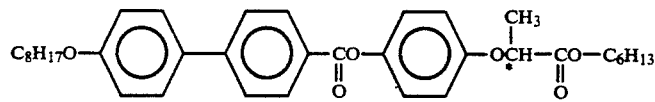
(44)
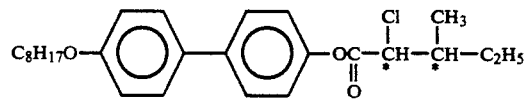
(45)
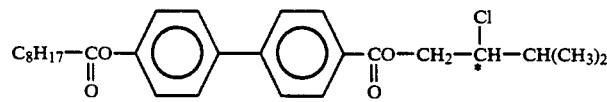
(46)

-continued
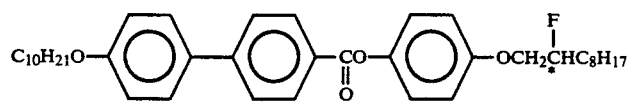 (47)
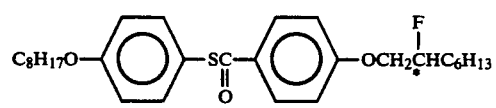 (48)
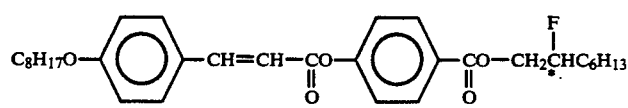 (49)
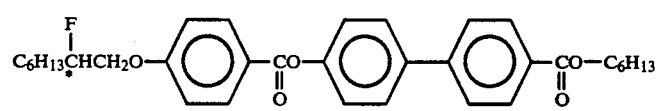 (50)
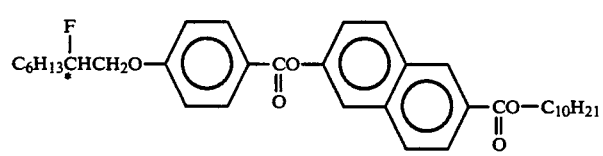 (51)
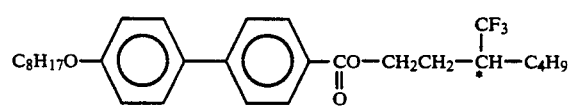 (52)
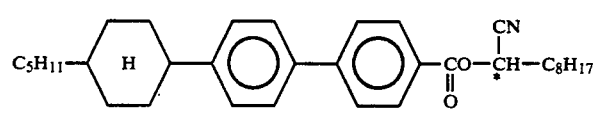 (53)
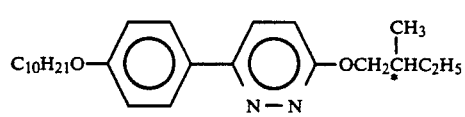 (54)
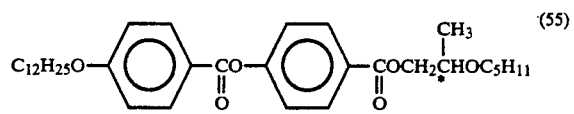 (55)
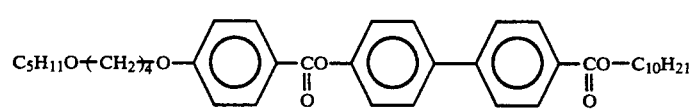 (56)
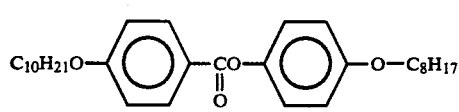 (57)
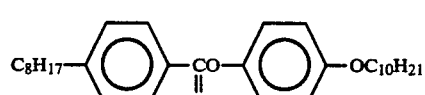 (58)
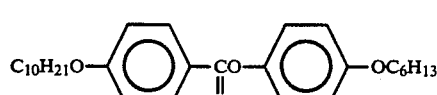 (59)
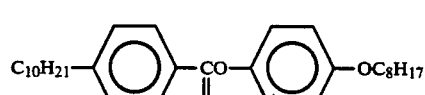 (60)
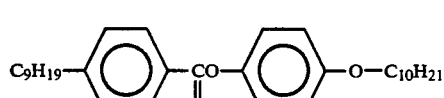 (61)
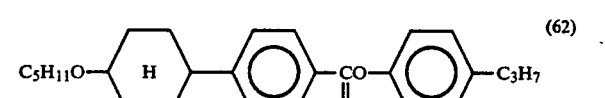 (62)
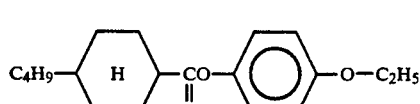 (63)

-continued

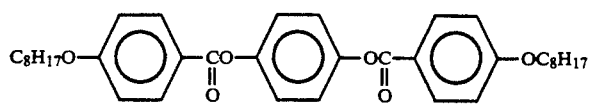 (64)

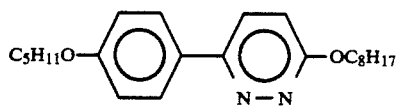 (65)
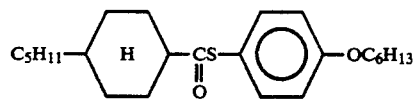 (66)

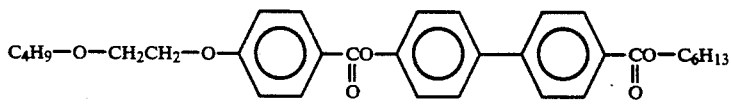 (67)

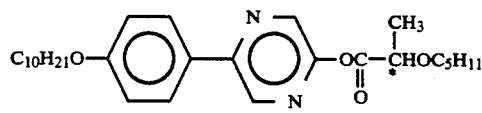 (68)

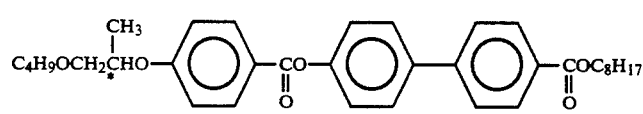 (69)

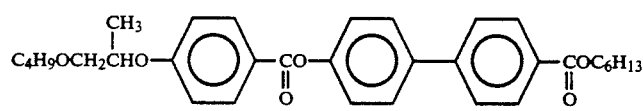 (70)

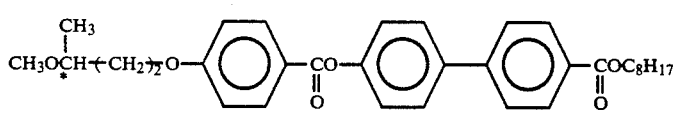 (71)

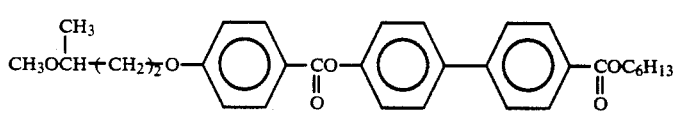 (72)

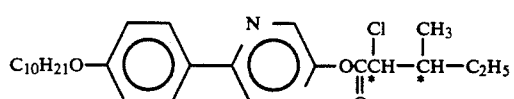 (73)

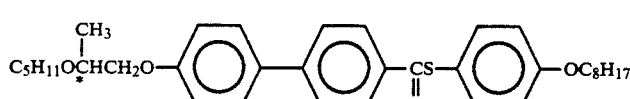 (74)

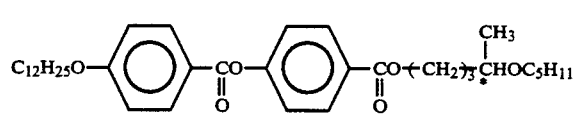 (75)

In formulating the liquid crystal composition according to the present invention, it is desirable to mix 1-300 wt. parts each, preferably 2-100 wt. parts each, of a compound represented by the formula (I) and a compound represented by the formula (II) with 100 wt. parts of another mesomorphic compound as mentioned above which can be composed of two or more species.

Further, when two or more species of either one or both of the compounds represented by the formulas (I) and (II) are used, the two or more species of the compound of the formula (I) or (II) may be used in a total amount of 1-500 wt. parts, preferably 2-100 wt. parts, per 100 wt. parts of another mesomorphic compound as described above which can be composed of two or more species.

Further, the weight ratio of the compound of the formula (I)/the compound of the formula (II) may desirably be 1/300-300/1, preferably 1/50-50/1. When two or more species each of the compounds of the formulas (I) and (II) are used, the weight ratio of the total amount of the compounds of the formula (I)/the total amounts of the compounds of the formula (II) may desirably be 1/500-500/1, preferably 1/50-50/1.

Further, the total amounts of the compounds of the formulas (I) and (II) may desirably be 2-600 wt. parts, preferably 4–200 wt. parts, when one species each is selected from the formulas (I) and (II), or 2–1000 1000 wt. parts, preferably 4–200 wt. parts, when two or more species are selected from at least one of the formulas (I) and (II), respectively, with respect to 100 wt. parts of the above-mentioned another mesomorphic compound which may be composed of two or more species.

Further, a mesomorphic compound having a negative dielectric anisotropy as described above can be contained in a proportion of 1–98 wt. % of the liquid crystal composition of the present invention so as to provide a composition having a negative dielectric anisotropy. Particularly, when a mesomorphic compound having $\Delta\epsilon < -2$ is used, it may be contained in a proportion of 1–70 wt. %, preferably 1–50 wt. %, of the liquid crystal composition of the present invention.

Further, the total of the compounds of the formulas (I) and (II) and the mesomorphic compound having a negative dielectric anisotropy can constitute 3–100 wt. % of the liquid crystal composition of the present invention.

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer.

An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the ferroelectric liquid crystal may show a phase transition series comprising isotropic phase - Ch phase (cholesteric phase - SmA phase (smectic A phase) - SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
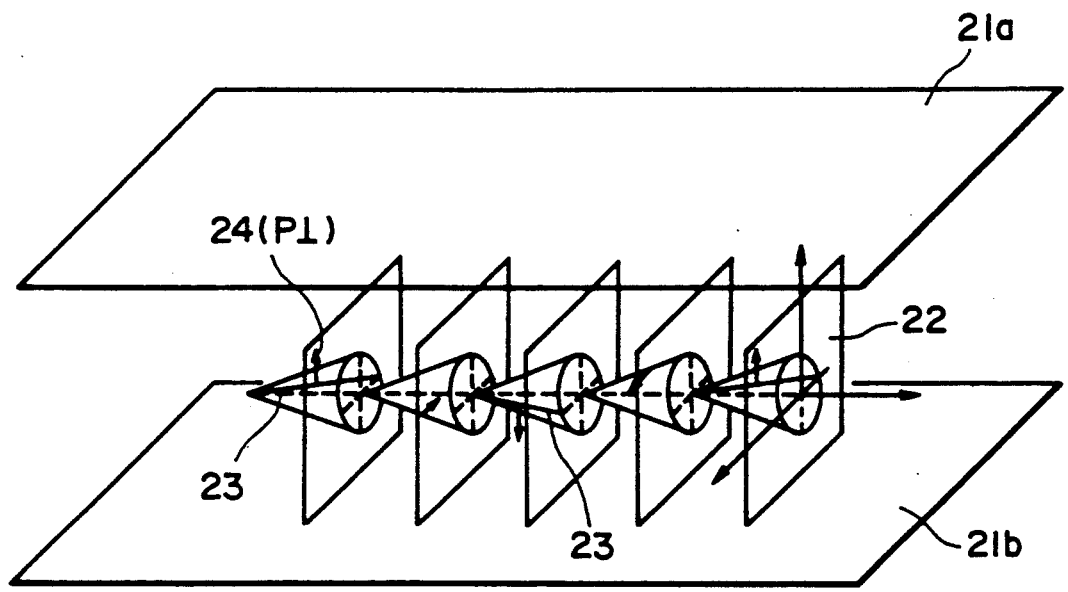
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
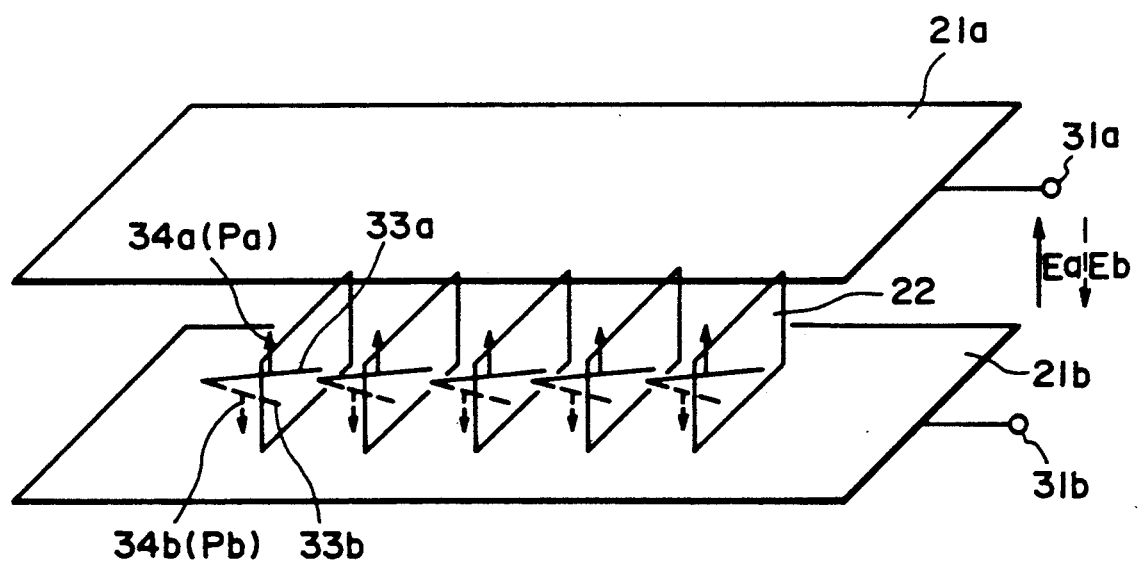
Figure 4:
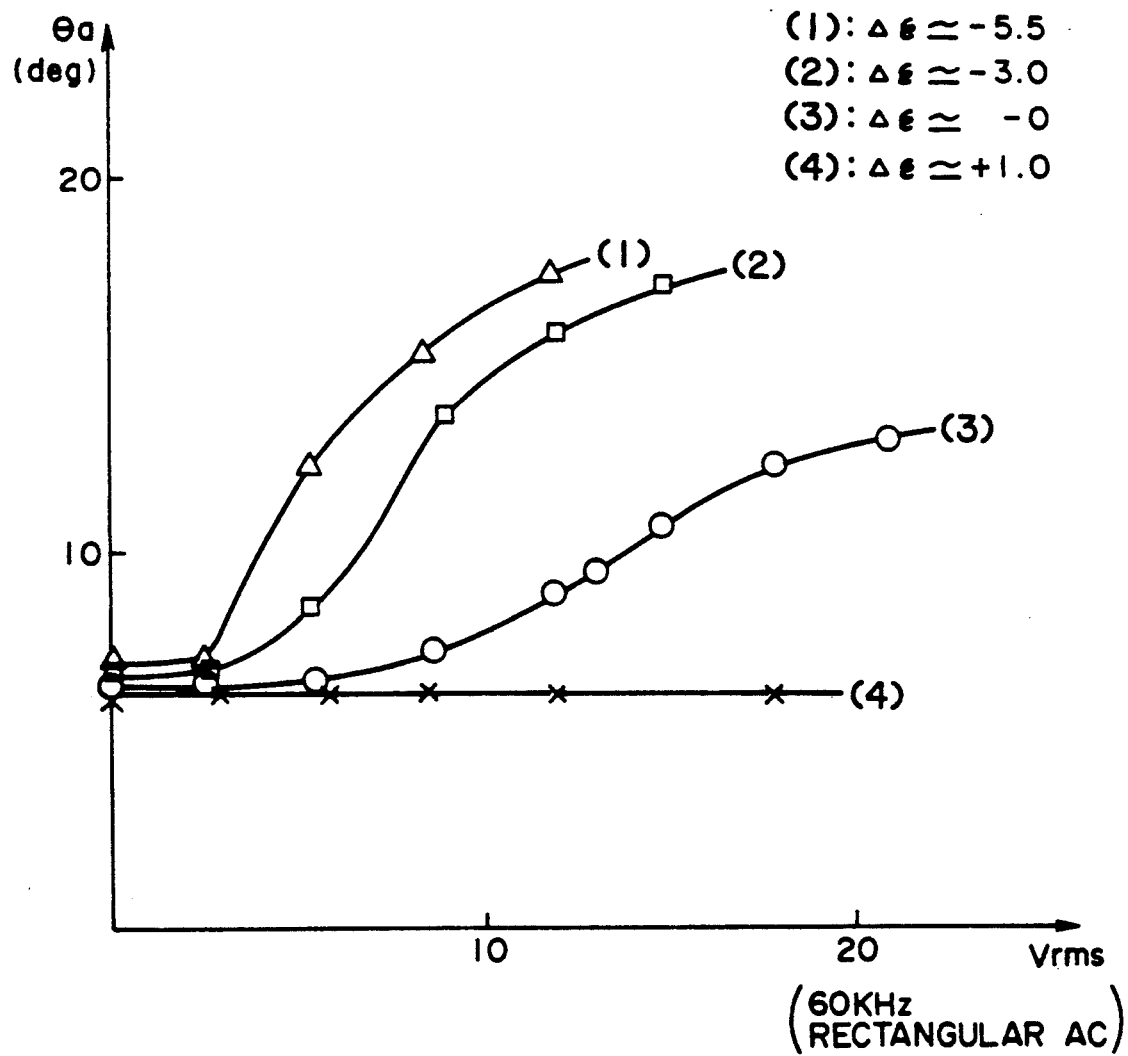
FIG. 4 is a graph showing changes in tilt angle $\theta a$ versus effective voltage Vrms with respect to several ferroelectric liquid crystals having different values of dielectric anisotropy $\Delta\epsilon$.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3.

When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

A liquid crystal composition 1-A was prepared by mixing the following compounds in respectively indicated proportions.

| Ex. Compound No. | Structural formula | Wt. parts |
|---|---|---|
| 24 | $C_{10}H_{21}O$—⌬—COS—⌬—$OCH_2\overset{*}{C}H(CH_3)OC_3H_7$ | 10 |
| 25 | $C_{12}H_{25}O$—⌬—COS—⌬—$OCH_2\overset{*}{C}H(CH_3)OC_8H_{17}$ | 20 |
| 67 | $C_4H_9OCH_2CH_2O$—⌬—COO—⌬—⌬—$COOC_6H_{13}$ | 10 |
| 4 | $C_2H_5\overset{*}{C}H(CH_3)CH_2$—⌬—⌬—COO—⌬—$OC_8H_{17}$ | 10 |
| 5 | $C_2H_5\overset{*}{C}H(CH_3)CH_2$—⌬—⌬—COO—⌬—$OC_6H_{13}$ | 20 |
| 57 | $C_{10}H_{21}O$—⌬—COO—⌬—$OC_8H_{17}$ | 15 |
| 58 | $C_8H_{17}$—⌬—COO—⌬—$OC_{10}H_{21}$ | 15 |

| Ex. Compound No. | Structural formula | Wt. parts |
|---|---|---|
| 47 | 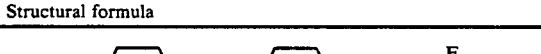 C$_{10}$H$_{21}$O—◯—◯—COO—◯—OCH$_2$$\overset{*}{C}$HC$_8$H$_{17}$ (F) | 5 |
| 51 | 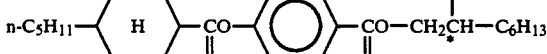 C$_6$H$_{13}$$\overset{*}{C}$HCH$_2$O—◯—COO—◯◯—COOC$_{10}$H$_{21}$ (F) | 5 |

A liquid crystal composition 1-B was prepared by mixing the following example compounds 1-3 and 2-8 with the above prepared composition 1-A.

| Ex. Comp. No. | Structural formula | Wt. parts |
|---|---|---|
| 1-3 | n-C$_5$H$_{11}$—⟨H⟩—CO—O—◯—CO—O—CH$_2$$\overset{*}{C}$H—C$_6$H$_{13}$-n (F) | 8 |
| 2-8 | n-C$_3$H$_7$—⟨H⟩—CO—O—◯—⟨N,N⟩—C$_{10}$H$_{21}$-n | 12 |
| Composition 1-A | | 80 |

The above-prepared liquid crystal composition 1-B was used to prepare a liquid crystal device in combination with a blank cell prepared in the following manner.

Two 1.1 mm-thick glass plates were provided and respectively coated with an ITO film to form an electrode for voltage application, which was further coated with an insulating layer of vapor-deposited SiO$_2$. The insulating layer was further coated with a 1.0 %-solution of polyimide resin precursor (SP-510, available from Toray K.K.) in dimethylacetoamide by a spinner coater rotating at 3000 rpm for 15 seconds. Thereafter, the coating film was subjected to heat curing at 300° C. for 60 min. to obtain about 120 Å-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 1.5 microns as measured by a Berek compensator.

Then, the above-prepared liquid crystal composition 1-B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of an optical response time (time from voltage application until the transmittance change reaches 90% of the maximum) at specified temperatures under the application of a peak-to-peak voltage Vpp of 25 volts. The results are shown below.

| | 10° C. | 25° C. | 40° C. |
|---|---|---|---|
| Response time | 365 μsec | 95 μsec | 35 μsec |

Further, a contrast of 13 was attained at 25° C. during the driving, and a clear switching function was observed.

COMPARATIVE EXAMPLE 1

A liquid crystal composition 1-C was prepared by omitting Example compound No. 1-3 from the liquid crystal composition 1-B, i.e., by adding only Example compound No. 2-8 to the liquid crystal composition 1-A, and a liquid crystal composition 1-D was prepared by omitting Example compound No. 2-8 from the composition 1-B, i.e., by adding only Example compound No. 1-3 to the composition 1-A.

Ferroelectric liquid crystal devices 1-A, 1-C and 1-D were prepared by using the compositions 1-A, 1-C and 1-D, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 1-A | 620 μsec | 170 μsec | 52 μsec |
| 1-C | 515 μsec | 140 μsec | 45 μsec |
| 1-D | 440 μsec | 120 μsec | 40 μsec |

As apparent from the above Example 1 and Comparative Example 1, the ferroelectric liquid crystal device containing the liquid crystal composition 1-B according to the present invention provided improved response speed and operation characteristic at a lower temperature and also provided a decreased temperature dependence of response speed (ratio of response time (10° C./40° C.)).

EXAMPLE 2

A liquid crystal composition 2-B was prepared by mixing the following example compounds in the indicated proportions with the liquid crystal composition 1-A prepared in Example 1.

| Ex. Comp. No. | Structural formula | wt. parts |
|---|---|---|
| 1-17 | 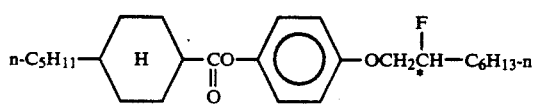 | 8 |
| 2-100 | 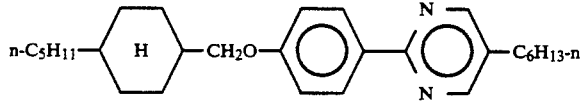 | 7 |
| 2-104 | 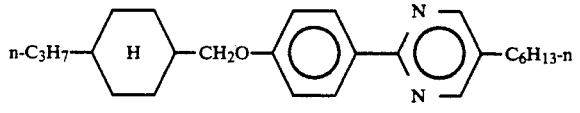 | 7 |
| | Composition 1-A | 78 |

A ferroelectric liquid crystal device was prepared in the same manner as in Example 1 except that the above liquid crystal composition 2-B was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 370 μsec | 93 μsec | 35 μsec |

Further, a contrast of 13 was attained at 25° C. during the driving, and a clear switching function was observed. The bistability after termination of the voltage application was also good.

COMPARATIVE EXAMPLE 2

A liquid crystal composition 2-C was prepared by omitting Example compound No. 1-17 from the liquid crystal composition 2-B, i.e., by adding only Example compounds Nos. 2-100 and 2-104 to the liquid crystal composition 1-A, and a liquid crystal composition 2-D was prepared by omitting Example compounds Nos. 2-100 and 2-104 from the composition 2-B, i.e., by adding only Example compound No. 1-17 to the composition 1-A.

Ferroelectric liquid crystal devices 2-C and 2-D were prepared by using the compositions 2-C and 2-D, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 2-C | 510 μsec | 135 μsec | 45 μsec |
| 2-D | 435 μsec | 125 μsec | 40 μsec |

As apparent from the above Example 2 and Comparative Example 2, the ferroelectric liquid crystal device containing the liquid crystal composition 2-B according to the present invention provided improved response speed and operation characteristic at a lower temperature and also provided a decreased temperature dependence of response speed.

EXAMPLE 3

A liquid crystal composition 3-B was prepared by mixing the following example compounds in the indicated proportions with the liquid crystal composition 1-A prepared in Example 1.

| Ex. Comp. No. | Structural formula | wt. parts |
|---|---|---|
| 1-22 | 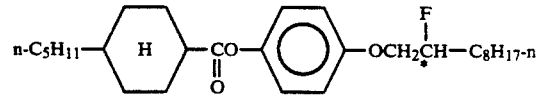 | 9 |

| Ex. Comp. No. | Structural formula | wt. parts |
|---|---|---|
| 2-9 | n-$C_5H_{11}$—[H]—CO—O—[phenyl]—[pyrimidine N,N]—$C_{11}H_{23}$-n | 6 |
| 2-12 | n-$C_3H_7$—[H]—CO—O—[phenyl]—[pyrimidine N,N]—$C_{11}H_{23}$-n | 6 |
| 2-15 | n-$C_4H_9$—[H]—CO—O—[phenyl]—[pyrimidine N,N]—$C_{10}H_{21}$-n | 6 |
| Composition 1-A | | 73 |

A ferroelectric liquid crystal device was prepared in the same manner as in Example 1 except that the above liquid crystal composition 3-B was used, and the device was subjected to measurement of driving voltage margin and observation of switching states. In the device, a monodomain with a good and uniform alignment characteristic was observed. The results of the measurement are shown below.

| | 10° C. | 25° C. | 40° C. |
|---|---|---|---|
| Response time | 355 μsec | 90 μsec | 35 μsec |

Further, a contrast of 13 was attained at 25° during the driving, and a clear switching function was observed. The bistability after termination of the voltage application was also good.

COMPARATIVE EXAMPLE 3

A liquid crystal composition 3-C was prepared by omitting Example compound No. 1-22 from the liquid crystal composition 3-B, i.e., by adding only Example compounds Nos. 2-9, 2-12 and 2-15 to the liquid crystal composition 1-A, and a liquid crystal composition 3-D was prepared by omitting Example compounds Nos. 2-9, 2-12 and 2-15 from the composition 3-B, i.e., by adding only Example compound No. 1-22 to the composition 1-A.

Ferroelectric liquid crystal devices 3-C and 3-D were prepared by using the compositions 3-C and 3-D, respectively, instead of the composition 1-B, and subjected to measurement of optical response time, otherwise in the same manner as in Example 1. The results are shown below.

| | Response time | | |
|---|---|---|---|
| | 10° C. | 25° C. | 40° C. |
| 3-C | 520 μsec | 140 μsec | 45 μsec |
| 3-D | 450 μsec | 130 μsec | 40 μsec |

As apparent from the above Example 3 and Comparative Example 3, the ferroelectric liquid crystal device containing the liquid crystal composition 3-B according to the present invention provided improved response speed and operation characteristic at a lower temperature and also provided a decreased temperature dependence of response speed.

EXAMPLE 4

A liquid crystal composition 4-A was prepared by mixing the following compounds in respectively indicated proportions.

| Ex. Compound No. | Structural formula | Wt. parts |
|---|---|---|
| 8 | $C_8H_{17}O$—[phenyl]—COS—[phenyl]—$CH_2\overset{*}{C}H(CH_3)C_2H_5$ | 40 |
| 9 | $C_{12}H_{25}O$—[phenyl]—COS—[phenyl]—$CH_2\overset{*}{C}H(CH_3)C_2H_5$ | 40 |
| 12 | $C_8H_{17}O$—[phenyl]—COS—[phenyl]—$OCH_2\overset{*}{C}H(CH_3)C_2H_5$ | 15 |

| Ex. Compound No. | Structural formula | Wt. parts |
|---|---|---|
| 13 | $C_{10}H_{21}O$-⬡-COS-⬡-$OCH_2\overset{*}{C}H(CH_3)C_2H_5$ | 15 |
| 17 | $C_8H_{17}O$-$\overset{*}{C}H(CH_3)CH_2O$-⬡-COO-⬡-⬡-$COOC_6H_{13}$ | 25 |
| 18 | $C_5H_{11}O\overset{*}{C}H(CH_3)CH_2O$-⬡-COO-⬡-⬡-$COOC_{10}H_{21}$ | 25 |
| 67 | $C_4H_9OCH_2CH_2O$-⬡-COO-⬡-⬡-$COOC_6H_{13}$ | 10 |
| 57 | $C_{10}H_{21}O$-⬡-COO-⬡-$OC_8H_{17}$ | 5 |
| 60 | $C_{10}H_{21}$-⬡-COO-⬡-$OC_8H_{17}$ | 5 |

A liquid crystal composition 4-B was prepared by mixing the following example compounds 1-10, 2-1 and 2-4 with the above prepared composition 4-A.

| Ex. Comp. No. | Structural formula | wt. parts |
|---|---|---|
| 1-10 | $CH_3$-[H]-CO-O-⬡-$OCH_2\overset{*}{C}H(F)$-$C_4H_9$-n | 7 |
| 2-1 | n-$C_3H_7$-[H]-CO-O-⬡-⬡-$OC_{10}H_{21}$ | 10 |
| 2-4 | n-$C_3H_7$-[H]-CO-O-⬡-[N,N pyrazine]-$C_{12}H_{25}$ | 10 |
| | Composition 4-A | 73 |

A ferroelectric liquid crystal device 4-B was prepared in the same manner as in Example 1 except that the liquid crystal composition 4-B was used instead of the composition 1-B. The device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 1280 μsec | 320 μsec | 120 μsec |

Further, a contrast of 12 was attained at 25° during the driving, and a clear switching function was observed.

COMPARATIVE EXAMPLE 4

A liquid crystal composition 4-C was prepared by omitting Example compound No. 1-10 from the liquid crystal composition 4-B prepared in Example 4, i.e., by adding only Example compounds Nos. 2-1 and 2-4 to the liquid crystal composition 4-A, and a liquid crystal composition 4-D was prepared by omitting Example compounds Nos. 2-1 and 2-4 from the composition 4-B, i.e., by adding only Example compound No. 1-10 to the composition 4-A.

Ferroelectric liquid crystal devices 4-A, 4-C and 4-D were prepared by using the compositions 4-A, 4-C and 4-D, respectively, instead of the composition 1-B, and subjected to measurement of optical response time, otherwise in the same manner as in Example 1. The results are shown below.

|     | Response time ($\mu$sec) | | |
| --- | --- | --- | --- |
|     | 10° C. | 25° C. | 40° C. |
| 4-A | 2000 | 530 | 158 |
| 4-C | 1800 | 465 | 145 |
| 4-D | 1620 | 400 | 135 |

As apparent from the above Example 4 and Comparative Example 4, the ferroelectric liquid crystal device containing the liquid crystal composition 4-B according to the present invention provided improved response speed and operation characteristic at a lower temperature and also provided a decreased temperature dependence of response speed.

EXAMPLE 5

A liquid crystal composition 5-B was prepared by mixing the following example compounds in the indicated proportions with the liquid crystal composition 4-A prepared in Example 4.

|       | 10° C. | 25°C. | 40° C. |
| --- | --- | --- | --- |
| Response time | 1250 $\mu$sec | 315 $\mu$sec | 115 $\mu$sec |

Further, a contrast of 13 was attained at 25° C. during the driving, and a clear switching function was observed. The bistability after termination of the voltage application was also good.

COMPARATIVE EXAMPLE 5

A liquid crystal composition 5-C was prepared by omitting Example compounds Nos. 1-3 and 1-16 from the liquid crystal composition 5-B, i.e., by adding only Example compound No. 2-73 to the liquid crystal composition 4-A, and a liquid crystal composition 5-D was prepared by omitting Example compound No. 2-73 from the composition 5-B, i.e., by adding only Example compounds Nos. 1-3 and 1-16 to the composition 4-A.

Ferroelectric liquid crystal devices 5-C and 5-D were prepared by using the compositions 5-C and 5-D, respectively, instead of the composition 1-B, and subjected to measurement of optical response time, otherwise in the same manner as in Example 1. The results are shown below.

|     | Response time ($\mu$sec) | | |
| --- | --- | --- | --- |
|     | 10° C. | 25° C. | 40° C. |
| 5-C | 1830 | 470 | 145 |
| 5-D | 1400 | 355 | 120 |

As apparent from the above Example 5 and Compar-

| Ex. Comp. No. | Structural formula | wt. parts |
| --- | --- | --- |
| 1-3 | n-C$_5$H$_{11}$–⟨H⟩–CO–O–⟨◯⟩–CO–O–CH$_2$CH*–C$_6$H$_{13}$-n (F) | 3 |
| 1-16 | n-C$_4$H$_9$–⟨H⟩–CO–O–⟨◯⟩–OCH$_2$CH*–C$_6$H$_{13}$-n (F) | 8 |
| 2-73 | n-C$_3$H$_7$–⟨H⟩–CH$_2$O–⟨◯⟩–⟨N◯N⟩–C$_{12}$H$_{25}$-n | 10 |
| Composition 4-A | | 79 |

A ferroelectric liquid crystal device was prepared in the same manner as in Example 1 except that the above liquid crystal composition 5-B was used, and the device was subjected to measurement of optical response time and observation of switching states. In the device, a monodomain with a good and uniform alignment characteristic was observed. The results of the measurement are shown below.

ative Example 5, the ferroelectric liquid crystal device containing the liquid crystal composition 5-B according to the present invention provided improved response speed and operation characteristic at a lower temperature and also provided a decreased temperature dependence of response speed.

EXAMPLE 6

A liquid crystal composition 6-A was prepared by mixing the following compounds in respectively indicated proportions.

| Ex. Compound No. | Structural formula | Wt. parts |
|---|---|---|
| 8 | 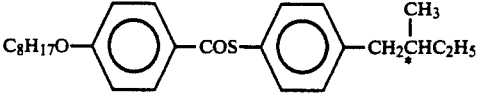 | 45 |
| 9 | 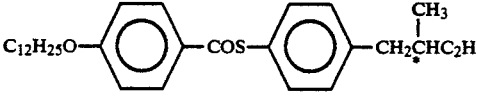 | 45 |
| 12 | 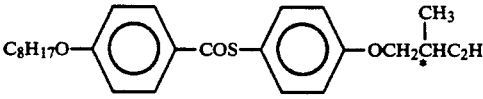 | 15 |
| 13 | 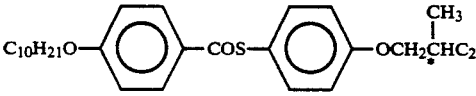 | 15 |
| 17 | 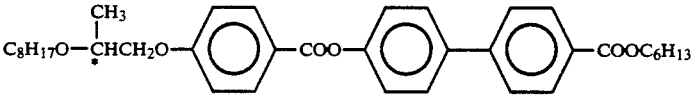 | 30 |
| 18 | 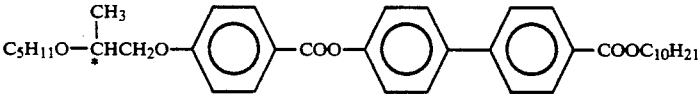 | 30 |
| 67 | 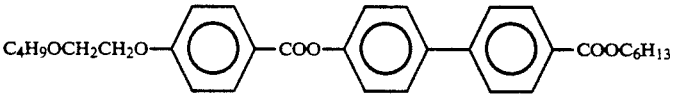 | 10 |

A liquid crystal composition 6-B was prepared by mixing the following example compounds 1-17, 2-12 and 2-16 with the above prepared composition 6-A.

| Ex. Comp. No. | Structural formula | Wt. parts |
|---|---|---|
| 1-17 | 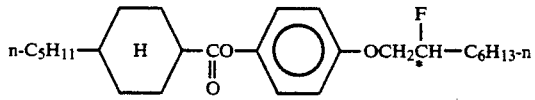 | 7 |
| 2-12 | 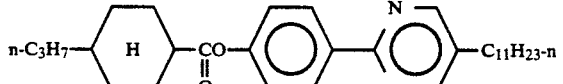 | 9 |
| 2-16 | 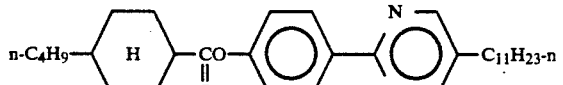 | 9 |
| Composition 6-A | | 75 |

A ferroelectric liquid crystal device 6-B was prepared in the same manner as in Example 1 except that the liquid crystal composition 6-B was used instead of the composition 1-B. The device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time | 1230 μsec | 330 μsec | 110 μsec |

Further, a contrast of 14 was attained at 25° C. during the driving, and a clear switching function was observed.

COMPARATIVE EXAMPLE 6

A liquid crystal composition 6-C was prepared by omitting Example compound No. 1-17 from the liquid crystal composition 6-B prepared in Example 6, i.e., by adding only Example compounds Nos. 2-12 and 2-16 to the liquid crystal composition 6-A, and a liquid crystal composition 6-D was prepared by omitting Example compounds Nos. 2-12 and 2-16 from the composition 6-B, i.e., by adding only Example compound No. 1-17 to the composition 6-A.

Ferroelectric liquid crystal devices 6-A, 6-C and 6-D were prepared by using the compositions 6-A, 6-C and 6-D, respectively, instead of the composition 1-B, and subjected to measurement of optical response time, otherwise in the same manner as in Example 1. The results are shown below.

|  | Response time ($\mu$sec) | | |
|---|---|---|---|
|  | 10° C. | 25° C. | 40° C. |
| 6-A | 1600 | 430 | 120 |
| 6-C | 1520 | 410 | 120 |
| 6-D | 1475 | 375 | 115 |

As apparent from the above Example 6 and Comparative Example 6, the ferroelectric liquid crystal device containing the liquid crystal composition 6-B according to the present invention provided improved response speed and operation characteristic at a lower temperature and also provided a decreased temperature dependence of response speed.

EXAMPLE 7

A liquid crystal composition 7-B was prepared by mixing the following example compounds in the indicated proportions with the liquid crystal composition 6-A prepared in Example 6.

A ferroelectric liquid crystal device was prepared in the same manner as in Example 1 except that the above liquid crystal composition 7-B was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time | 1210 $\mu$sec | 325 $\mu$sec | 110 $\mu$sec |

Further, a contrast of 11 was attained at 25° C. during the driving, and a clear switching function was observed. The bistability after termination of the voltage application was also good.

COMPARATIVE EXAMPLE 7

A liquid crystal composition 7-C was prepared by omitting Example compound No. 1-25 from the liquid crystal composition 7-B prepared in Example 7, i.e., by adding only Example compound No. 2-66 to the liquid crystal composition 6-A, and a liquid crystal composition 7-D was prepared by omitting Example compound No. 2-66 from the composition 7-B, i.e., by adding only Example compound No. 1-25 to the composition 6-A.

Ferroelectric liquid crystal devices 7-C and 7-D were prepared by using the compositions 7-C and 7-D, respectively, instead of the composition 1-B, and subjected to measurement of optical response time, otherwise in the same manner as in Example 1. The results are shown below.

|  | Response time ($\mu$sec) | | |
|---|---|---|---|
|  | 10° C. | 25° C. | 40° C. |
| 7-C | 1560 | 405 | 120 |
| 7-D | 1430 | 365 | 115 |

As apparent from the above Example 7 and Comparative Example 7, the ferroelectric liquid crystal device containing the liquid crystal composition 7-B according to the present invention provided improved response speed and operation characteristic at a lower temperature and also provided a descreased temperature dependence of response speed.

EXAMPLES 8-15

| Ex. Comp. No. | Structural formula | wt. parts |
|---|---|---|
| 1-25 | n-C$_5$H$_{11}$—⟨H⟩—CO—⟨⟩—OCH$_2$$\overset{*}{C}$HC$_2$H$_5$ (with F) | 8 |
| 2-66 | n-C$_3$H$_7$—⟨H⟩—OC(=O)—⟨⟩—⟨⟩—CH$_2$$\overset{*}{C}$HC$_2$H$_5$ (with CH$_3$) | 15 |
| Composition 6-A |  | 77 |

Liquid crystal compositions 8-B to 15-B were prepared by replacing the example compounds and the liquid crystal compositions used in Examples 1, 4 and 6 with example compounds and liquid crystal compositions shown in the following Table 1. Ferroelectric liquid crystal devices were prepared by respectively using these compositions instead of the composition 1-B, and subjected to measurement of optical response time and observation of switching states. In the devices, a monodomain with a good and uniform alignment characteristic was observed. The results of the measurement are shown in the following Table 1.

TABLE 1

| Ex. No. (Comp. No.) | Example compound No. or liquid crystal composition No. (weight parts) | | | | | Response time (μsec) | | |
|---|---|---|---|---|---|---|---|---|
| | | | | | | 10° C. | 25° C. | 40° C. |
| 8 (8-B) | 1-17 (8) | 2-20 (5) | 2-24 (10) | | 1-A (77) | 410 | 108 | 40 |
| 9 (9-B) | 1-3 (4) | 1-6 (4) | 2-77 (10) | 2-79 (5) | 1-A (77) | 415 | 110 | 40 |
| 10 (10-B) | 1-17 (6) | 2-9 (4) | 2-12 (8) | 2-16 (4) | 4-A (78) | 1210 | 300 | 110 |
| 11 (11-B) | 1-15 (4) | 1-22 (4) | 2-26 (5) | 2-37 (5) | 2-49 (5) 4-A (77) | 1280 | 315 | 120 |
| 12 (12-B) | 1-17 (8) | 2-100 (10) | 2-104 (12) | | 4-A (70) | 1250 | 310 | 115 |
| 13 (13-B) | 1-4 (4) | 1-8 (5) | 2-82 (10) | 2-93 (15) | 6-A (66) | 1180 | 315 | 105 |
| 14 (14-B) | 1-15 (4) | 1-17 (2) | 1-21 (2) | 2-55 (8) | 2-67 (10) 6-A (74) | 1200 | 305 | 110 |
| 15 (15-B) | 1-3 (3) | 1-21 (8) | 2-69 (3) | 2-73 (3) | 2-100 (10) 6-A (73) | 1120 | 300 | 100 |

As is apparent from the results shown in the above Table 1, the ferroelectric liquid crystal devices containing the liquid crystal compositions 8-B to 15-B provided improved response speed and a decreased temperature dependence of the response speed.

EXAMPLE 16

A liquid crystal composition 16-B was prepared by mixing the following example compound in the indicated proportion with the liquid crystal composition 1-B prepared in Example 1.

| Ex. Comp. No. | Structural formula | wt. parts |
|---|---|---|
| 3-10 | n-$C_5H_{11}$—(H)—CO—(CN)(CN)—$OC_6H_{13}$-n | 10 |
| | Composition 1-B | 90 |

A ferroelectric liquid crystal device was prepared in the same manner as in Example 1 except that the above liquid crystal composition was used, and the device was subjected to measurement of optical response time in the same manner as in Example 1 to obtain the following results.

| Response time | | |
|---|---|---|
| 10° C. | 25° C. | 40° C. |
| 438 μsec | 107 μsec | 39 μsec |

Then, the tilt angle of the above device measured under right-angle cross nicols at 25° C. to provide 7.8 degrees. Further, the tilt angle of the device was again measured while being subjected to application of rectangular waveforms of ±8 V and a frequency of 60 KHz and found to be 13.7 degrees. The transmittance measured at that time was 14.0%, and a contrast of 70:1 was attained.

COMPARATIVE EXAMPLE 16

A liquid crystal composition 16-C was prepared in the same manner as in Example 16 except that the liquid crystal composition 1-A prepared in Example 1 was used instead of the composition 1-B to be mixed with the example compound No. 3-10 in the same proportions.

Ferroelectric liquid crystal devices were prepared by using the compositions 16-C, 1-A and 1-B respectively and subjected to measurement of optical response time, otherwise in the same manner as in Example 1. Further, the tilt angles of these devices were measured in the same manner as in Example 16. The results are shown below.

| | Response time | | |
|---|---|---|---|
| | 10° C. | 25° C. | 40° C. |
| 1-A | 620 μsec | 170 μsec | 52 μsec |
| 1-B | 365 μsec | 95 μsec | 35 μsec |
| 16-C | 772 μsec | 210 μsec | 60 μsec |

| | Tilt angle (25° C.) | |
|---|---|---|
| Comp. | Initial (no electric field) | Under AC appln. (60 KHz, ±8 V, rectangular) |
| 1-A | 7.8 degrees | 8.0 degrees |
| 1-B | 7.7 degrees | 7.8 degrees |
| 16-C | 8.0 degrees | 13.7 degrees |

As apparent from Example 16 and Comparative Example 16, the liquid crystal composition 16-B obtained by mixing a mesomorphic compound having a negative dielectric anisotropy (example compound No. 3-10) with the liquid crystal composition 1-B according to the present invention provided an improved response characteristic and also provided a remarkably improved display characteristic when used in a display method utilizing AC application (or AC stabilization).

EXAMPLE 17

A liquid crystal composition 17-B was prepared by mixing the following example compounds in the respectively indicated proportions with the liquid crystal composition 1-B prepared in Example 1.

| Ex. Comp. No. | Structural formula | wt. parts |
|---|---|---|
| 3-90 | n-$C_{10}H_{21}$—[N=N, S thiadiazole]—⟨phenyl⟩—$OC_{12}H_{25}$-n | 5 |
| 3-12 | n-$C_8H_{17}$—⟨H cyclohexyl⟩—CO-O—⟨phenyl with CN, CN⟩—$OC_8H_{17}$-n | 5 |
| 3-122 | n-$C_8H_{17}$—⟨H cyclohexyl⟩—⟨H cyclohexyl with CN⟩—$C_8H_{17}$-n | 2 |
| 3-70 | n-$C_6H_{13}$—[phenyl, N=N]—⟨phenyl⟩—$OC_5H_{11}$-n | 3 |
| 3-107 | n-$C_{10}H_{21}$—[N=N, S thiadiazole]—⟨phenyl⟩—O-CO—⟨H cyclohexyl⟩—$C_3H_7$-n | 3 |
| 3-111 | n-$C_{12}H_{25}$—[N=N, S thiadiazole]—⟨phenyl⟩—$OCH_2$—⟨H cyclohexyl⟩—$C_5H_{11}$-n | 1 |
| 3-167 | n-$C_9H_{19}O$—⟨phenyl⟩—CH=C(CN)—⟨phenyl⟩—$C_7H_{15}$-n | 1 |
| Composition 1-B | | 80 |

A ferroelectric liquid crystal device was prepared in the same manner as in Example 1 except that the above liquid crystal composition was used, and the device was subjected to measurement of optical response time int he same manner as in Example 1 to obtain the following results.

|  | 10° C. | 25° C. | 40° C. |
|---|---|---|---|
| Response time | 432 μsec | 108 μsec | 40 μsec |

Then, the tilt angle of the above device was measured under right-angle cross nicols at 25° C. to provide 8.5 degrees. Further, the tilt angle of the device was again measured while being subjected to application of rectangular waveforms of ±8 V and a frequency of 60 KHz and found to be 14.2 degrees. The transmittance measured at that time was 14.9%, and a contrast of 59:1 was attained.

COMPARATIVE EXAMPLE 17

A liquid crystal composition 17-C was prepared in the same manner as in Example 17 except that the liquid crystal composition 1-A prepared in Example 1 was used instead of the composition 1-B to be mixed with the other example compounds in the same proportions.

Ferroelectric liquid crystal devices were prepared by using the compositions 17-C, 1-A and 1-B respectively and subjected to measurement of driving voltage margin, otherwise in the same manner as in Example 1. Further, the tilt angles of these devices were measured in the same manner as in Example 17. The results are shown below.

|  | Response time | | |
|---|---|---|---|
|  | 10° C | 25° C. | 40° C. |
| 1-A | 620 μsec | 170 μsec | 52 μsec |
| 1-B | 365 μsec | 95 μsec | 35 μsec |
| 17-C | 775 μsec | 207 μsec | 62 μsec |

| | Tilt angle (25° C.) | |
|---|---|---|
| Comp. | Initial (no electric field) | Under AC appln. (60 KHz, ±8 V, rectangular) |
| 1-A | 7.8 degrees | 8.0 degrees |
| 1-B | 7.7 degrees | 7.8 degrees |
| 17-C | 9.0 degrees | 13.7 degrees |

As apparent from Example 17 and Comparative Example 17, the liquid crystal composition 17-B obtained by mixing mesomorphic compounds having a negative dielectric anisotropy with the liquid crystal composition 1-B according to the present invention provided an improved responsive characteristic and also provided a remarkably improved display characteristic when used in a display method utilizing AC application (or AC stabilization).

EXAMPLE 18

A blank cell was prepared in the same manner as in Example 1 except for omitting the $SiO_2$ layer to form an alignment control layer composed of the polyimide resin layer alone on each electrode plate. Four ferroelectric liquid crystal devices were prepared by filling such a blank cell with liquid crystal compositions 1-B, 1-A, 1-C and 1-D, respectively, prepared in Example 1 and Comparative Example 1. These liquid crystal devices were subjected to measurement of optical response time in the same manner as in Example 1. The results are shown below.

|     | Response time ($\mu$sec) |       |       |
| --- | --- | --- | --- |
|     | 10° C. | 25° C. | 40° C. |
| 1-B | 355 | 90  | 35  |
| 1-C | 510 | 135 | 40  |
| 1-D | 420 | 120 | 40  |
| 1-A | 600 | 160 | 50  |

As is apparent from the above Example 18, also in the case of a different device structure, the device containing the ferroelectric liquid crystal composition 1-B according to the present invention provided improved operation characteristic at a lower temperature and also a decreased temperature dependence of response speed.

For example, the electric anisotropy $\Delta\epsilon$ of a mesomorphic compound or a liquid crystal composition referred to herein may be measured in the following manner.

A 5 micron-thick homogeneous alignment cell having an electrode of 0.7 cm² in area and a homogeneous alignment layer (rubbed polyimide) on both substrates, and a 5 micron-thick homeotropic alignment cell having an electrode of 0.7 cm² in area and a homeotropic alignment layer (aligning agent: "ODS-E" available from Chisso K.K.) on both substrates, are provided. The respective cells are filled with a sample liquid crystal material (compound or composition) to prepare liquid crystal devices. The capacitances of the liquid crystal layers are measured by applying a sine wave with a frequency of 100 KHz and amplitudes of $\pm 0.5$ V to the respective devices at a prescribed temperature set for the liquid crystal material, and the dielectric constants $\Delta_{\parallel}$ and $\Delta_{\perp}$ are obtained from the measured capacitance values of the respective devices, whereby the dielectric anisotropy $\Delta\epsilon$ is calculated by the equation of $\Delta\epsilon = \Delta_{\parallel} - \Delta_{\perp}$.

As described hereinabove, the ferroelectric liquid crystal composition according to the present invention provides a liquid crystal device which shows a good switching characteristic, an improved operation characteristic and a decreased temperature dependence of response speed. Further, the liquid crystal composition according to the present invention further containing a mesomorphic compound having a negative dielectric anisotropy, provides a liquid crystal device which retains the above-mentioned characteristics and further shows a remarkably improved display characteristic when used in a driving method utilizing AC stabilization.

What is claimed is:

1. A ferroelectric chiral smectic liquid crystal composition, comprising:

at least one compound represented by the following formula (I):

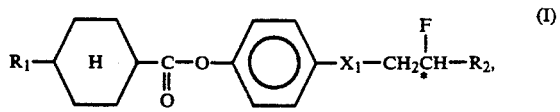

wherein $R_1$ denotes a linear alkyl group having 1-14 carbon atoms; $R_2$ denotes a linear or branched alkyl group having 1-14 carbon atoms; and $X_1$ denotes a single bond,

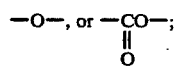

and at least one compound represented by the following formula (II):

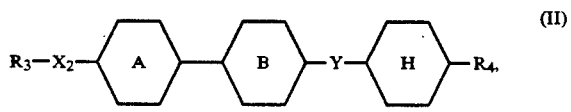

wherein $R_3$ denotes an unsubstituted linear or branched alkyl group having 1-18 carbon atoms optionally substituted with alkoxy group, alkoxy carbonyl group, Cl radical or F radical; $R_4$ denotes an unsubstituted linear alkyl group having 1-10 carbon atoms; $X_2$ denotes a single bond,

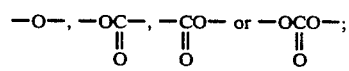

Y denotes $-OC-$, $-CO-$, $-CH_2O-$ or $-OCH_2-$;
                    ‖           ‖
                    O           O

2. A composition according to claim 1, which further comprises a mesomorphic compound having a negative dielectric anisotropy.

3. A composition according to claim 2, wherein said mesomorphic compound has a dielectric anisotropy $\Delta\epsilon$ of below $-2$.

4. A composition according to claim 3, wherein said mesomorphic compound has a dielectric anisotropy $\Delta\epsilon$ of below $-5$.

5. A composition according to claim 4, wherein said mesomorphic compound has a dielectric anisotropy $\Delta\epsilon$ of below $-10$.

6. A composition according to claim 2, wherein said mesomorphic compound having a negative dielectric anisotropy is a mesomorphic compound represented by any of the following formulas (III-1) to (III-5);

Formula (III-1):

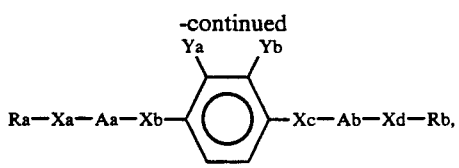

wherein Ra and Rb respectively denote a linear or branched alkyl group wherein Rb is optionally substituted with alkoxy group; Xa and Xd respectively denote a single bond,

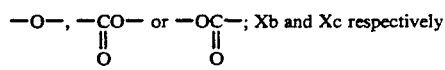

denote a single bond, —CO—, —OC— or —CH$_2$CH$_2$—;
         ‖         ‖
         O         O Aa and Ab respectively denote a single bond,

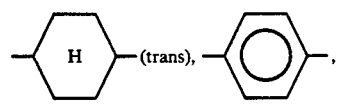

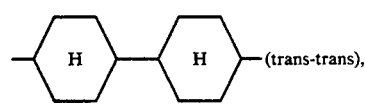

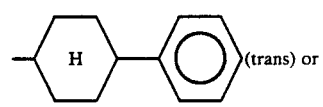

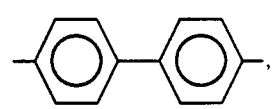

with proviso that when Aa and Ab are both single bonds, Xb and Xc are both single bonds, and Xa and Xd are both single bonds or —O—, or

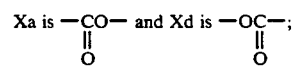

and Ya and Yb are respectively cyano group, halogen or hydrogen with proviso that Ya and Yb cannot be hydrogen simultaneously;

Formula (III-2):

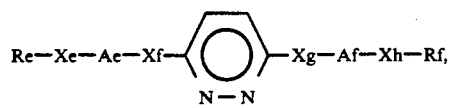

wherein Re and Rf respectively denote a linear or branched alkyl group; Xe and Xh are respectively a single bond,

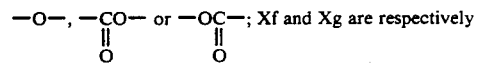

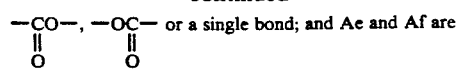

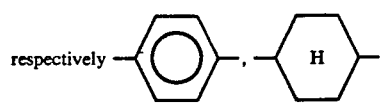

or a single bond with proviso that Ae and Af cannot be a single bond simultaneously;

Formula (III-3):

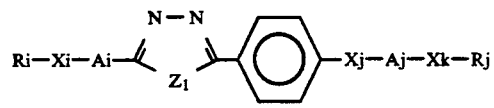

wherein Ai is a single bond or 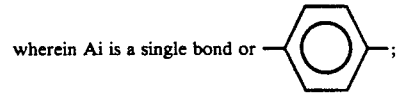;

Aj is a single bond, 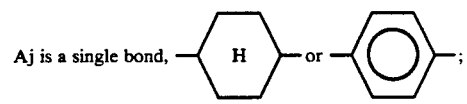;

Ri and Rj are respectively a linear or branched alkyl group wherein Ri is optionally substituted with Cl radical and Rj is optionally substituted with alkoxy group with proviso that Ri and Rj are linear alkyl groups when Aj is a single bond; Z$_1$ is —O— or —S—; Xi and Xk are respectively a single bond,

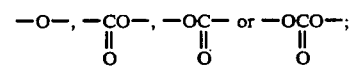

Xj is a single bond, —CO— —OC—,
              ‖     ‖
              O     O

—CH$_2$O— or —OCH$_2$—with proviso that Xi is a single bond when Ai is a single bond, Xj is not a single bond when Aj is

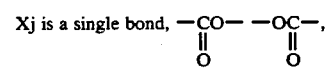

and Xk is a single bond when Aj is a single bond;

Formula (III-4):

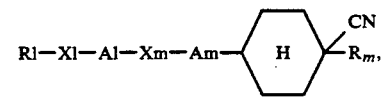

wherein Rl and Rm are respectively a linear or branched alkyl group; Al and Am are respectively a single bond,

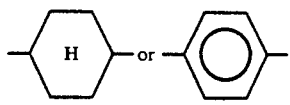

or with proviso that Al and Am cannot be a single bond simultaneously; Xl is a single bond, —O—, —CO—  or —OC—; and Xm is a single bond,
          ‖              ‖
          O              O

—CO—, —OC—, —CH₂O—, —OCH₂—,
 ‖      ‖
 O      O

—CH₂CH₂— or —C≡C—;

wherein Rn and Ro are respectively a linear or branched alkyl group; Xn and Xq are respectively a single bond, —O—, —CO— or —OC—; Xo and Xp are respectively
      ‖         ‖
      O         O a single bond, —CO—, —OC—, —CH₂O—,
                ‖      ‖
                O      O —OCH₂— or —CH₂CH₂—; An and Ap are respectively a single bond, 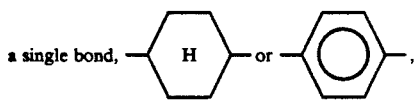

Ao is <img> ; and

Z₂ is —C=CH— or —CH—CH₂—.
       |            |
       CN           CN

7. A liquid crystal device, comprising a pair of electrode plates and a ferroelectric liquid crystal composition according to any one of claims 1-6 disposed between the electrode plates.

* * * * *

UNITED STATES PATENT AND TRADEMARK OFFICE
CERTIFICATE OF CORRECTION

PATENT NO. : 5,238,601
DATED : August 24, 1993
INVENTOR(S) : Kenji Shinjo, et al.

It is certified that error appears in the above-identified patent and that said Letters Patent is hereby corrected as shown below:

On the Title page

IN [30] FOREIGN APPLICATION PRIORITY DATA

Insert: --Jun. 9, 1989 [JP] Japan ....... 1-147988--.

COLUMN 7

Line 68, "include" should read --include —O— and —CO—.--.

COLUMN 8

Lines 1-41 should be deleted.

COLUMN 25

Line 39, "Yield: 64.8%." should read

--Yield: 64.8%.

Phase transition temperature (°C.)--.

COLUMN 33

Formula (3-40), 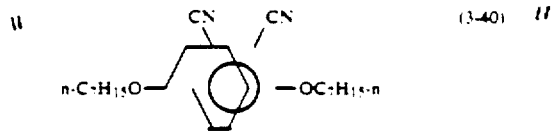

should read 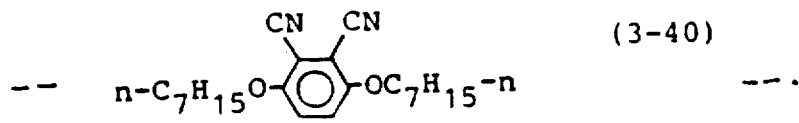

UNITED STATES PATENT AND TRADEMARK OFFICE
CERTIFICATE OF CORRECTION

PATENT NO. : 5,238,601
DATED : August 24, 1993
INVENTOR(S) : Kenji Shinjo, et al.

It is certified that error appears in the above-identified patent and that said Letters Patent is hereby corrected as shown below:

COLUMN 33

Formula (3-42), "  "

should read

-- 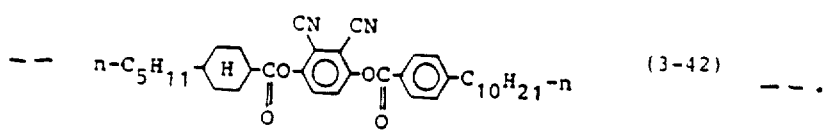 --.

COLUMN 34

Formula (3-39), " 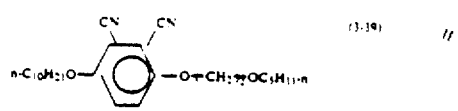 "

should read

-- 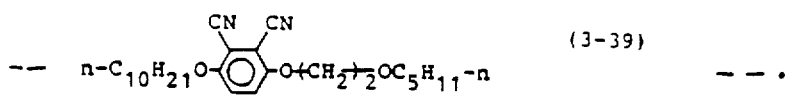 --.

COLUMN 34

Formula (3-41), " 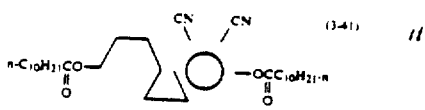 "

should read -- 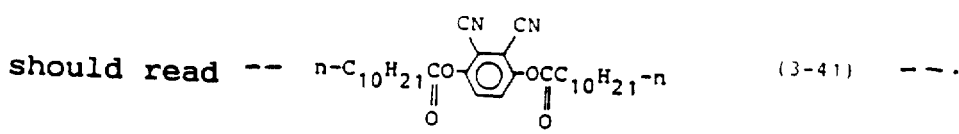 --.

UNITED STATES PATENT AND TRADEMARK OFFICE
CERTIFICATE OF CORRECTION

PATENT NO. : 5,238,601
DATED : August 24, 1993
INVENTOR(S) : Kenji Shinjo, et al.

It is certified that error appears in the above-identified patent and that said Letters Patent is hereby corrected as shown below:

COLUMN 59

Line 2, "2-1000 1000" should read --2-1000--.

COLUMN 67

Line 36, "25°" should read --25°C.--.

COLUMN 70

Line 61, "25°" should read --25°C.--.

COLUMN 79

Line 44, "int" should read in--.
Line 45, "he" should read --the--.

COLUMN 81

Line 47, "$\Delta_\parallel$ and $\Delta_\perp$" should read --$\epsilon_\parallel$ and $\epsilon_\perp$--.
Line 50, "$\Delta\epsilon = \Delta_\parallel - \Delta_\perp$" should read --$\Delta\epsilon = \epsilon_\parallel - \epsilon_\perp$--.

COLUMN 82

Line 26, "atoms" should read --atoms;--.
Line 27 should be deleted.
Line 28, "carbonyl group, Cl radical or F radical;" should be deleted.

UNITED STATES PATENT AND TRADEMARK OFFICE
CERTIFICATE OF CORRECTION

PATENT NO. : 5,238,601
DATED : August 24, 1993
INVENTOR(S) : Kenji Shinjo, et al.

It is certified that error appears in the above-identified patent and that said Letters Patent is hereby corrected as shown below:

COLUMN 85

Line 22, "$-CH_2CH_2-$ or $-C\equiv C-$;" should read

-- $-CH_2CH_2-$ or $-C\equiv C-$;

Formula (III-5):

Column 85

Line 9, "or" before "with" should be deleted.

Signed and Sealed this

Seventeenth Day of May, 1994

BRUCE LEHMAN

*Attest:*

*Attesting Officer*    *Commissioner of Patents and Trademarks*